United States Patent [19]
Brook et al.

[11] Patent Number: 5,977,333
[45] Date of Patent: *Nov. 2, 1999

[54] DNA SEQUENCE ENCODING THE MYOTONIC DYSTROPHY GENE AND USES THEREOF

[75] Inventors: J. David Brook, West Bridgford, United Kingdom; David E. Housman, Newton, Mass.; Duncan J. Shaw, Banchory, United Kingdom; Helen G. Harley, Rhiwbina, United Kingdom; Keith J. Johnson, Glasgow, United Kingdom

[73] Assignees: Massachusetts Institute of Technology, Cambridge, Mass.; University of Wales College of Medicine, Cardiff, United Kingdom

[*] Notice: This patent is subject to a terminal disclaimer.

[21] Appl. No.: 08/422,706

[22] Filed: Apr. 14, 1995

Related U.S. Application Data

[63] Continuation-in-part of application No. 08/284,543, filed as application No. PCT/GB93/00253, Feb. 5, 1993, abandoned, and a continuation-in-part of application No. 08/023,612, Feb. 26, 1993, abandoned, which is a continuation-in-part of application No. 07/839,255, Feb. 20, 1992, abandoned.

[30] Foreign Application Priority Data

Feb. 6, 1992 [GB] United Kingdom .................... 9202485
Feb. 19, 1993 [WO] WIPO ...................... PCT/US93/01545

[51] Int. Cl.$^6$ .......................... C07H 21/04; C07H 21/02; C12P 19/34; C12Q 1/68
[52] U.S. Cl. .................... 536/23.2; 536/24.3; 536/24.33; 536/23.5; 435/6; 435/91.2; 935/6; 935/8; 935/9; 935/78
[58] Field of Search .................................. 536/23.5, 24.3, 536/24.33; 935/6, 8, 9, 78; 435/6, 91.2

[56] References Cited

U.S. PATENT DOCUMENTS 5,387,506 2/1995 Blumenfeld et al. ........................ 435/6

FOREIGN PATENT DOCUMENTS

0614977A2 3/1994 European Pat. Off. .
93/16196 8/1993 WIPO .

OTHER PUBLICATIONS

G. Jansen et al. "Characterization of the myotonic dystrophy region predicts multiple protein isoform–encoding mRNAs" Nature Genetics Jul. 1992 (1)261–266.

H.J.M. Smeets et al. "Identification of Variable Simple Sequence Motifs in 19q 13.2–qter:Markers for the Myotonic Dystrophy Locus" Genomics Feb. 1991 (9)257–263.

Ausubel et al eds "Short Protocols in Molecular Biology" (1989) John Wiley and Sons, New York pp. 172–178, 190–194, and 201–231.

(List continued on next page.)

*Primary Examiner*—Stephanie W. Zitomer
*Assistant Examiner*—Deborah G. Shoemaker
*Attorney, Agent, or Firm*—Hamilton, Brook, Smith & Reynolds, P.C.

[57] ABSTRACT

A nucleotide sequence, specifically a CTG triplet repeat, is shown to be expanded in individuals affected with myotonic dystrophy and can be identified in a sample obtained from an individual. Individuals in whom the CTG triplet repeat is present in normal copy number are likely to be minimally affected and individuals in whom the CTG triplet repeat occurs in abnormally high copy number are likely to be more severely affected.

15 Claims, 22 Drawing Sheets

OTHER PUBLICATIONS

Mahadevan, M.S., et al., "Structure and Genomic Sequence of the Myotonic Dystrophy (DM Kinase) Gene," *Hum. Mol. Genet.,* 2 (3) :299–304 (1993).

Harley, H.G., et al., "Expansion of an unstable DNA region and phenotypic variation in myotonic dystrophy," *NATURE,* 355:545–546 (1992).

Buxton, J. et al,, "Detection of an unstable fragment of DNA specific to individuals with myotonic dystrophy," *NATURE,* 355: 547–548 (1992).

Aslanidis, C., et al., "Cloning of the essential myotonic dystrophy region and mapping of the putative defect," *NATURE,* 355: 548–551 (1992).

Sabouri, Luc A., et al., "Effect of the myotonic dystrophy (DM) mutation on mRNA levels of the DM gene," *NATURE GENETICS* 4:233–238 (Jul. 1993).

Wang, Yuh–Hwa, et al., "Preferential Nucleosome Assembly at DNA Triplet Repeats from the Myotonic Dystrophy Gene," *SCIENCE* 265:669–671 (Jul. 29, 1994).

Roses, A.D., and Appel, S. H., "Muscle membrane protein kinase in myotonic muscular dystrophy," *NATURE,* 250:245–247 (1974).

Willems, Patrick J., "Dynamic mutations hit double figures," *NATURE GENETICS* 8:213–215 (Nov. 1994).

Brook, J.D., et al., "Molecular Basis of Myotonic Dystrophy: Expansion of a Trinucleotide (CTG) Repeat at the 3' End of a Transcript Encoding a Protein Kinase Family Member," *CELL,* 68: 799–808 (1992).

Fu, Y.–H., et al., "An Unstable Triplet Repeat in a Gene Related to Myotonic Muscular Dystrophy," *SCIENCE,* 255:1256–1258 (1992).

Caskey, C.T., et al., "Triplet Repeat Mutations in Human Disease," *SCIENCE,* 256:784–788 (1992).

Tsilfidis, C., et al., "D19S51 is Closely Linked with and Maps Distal to the Myotonic Dystrophy Locus on 19q", *AM. J. HUM. GENET.,* 49:961–965 (1991).

Smeets, H., et al., "A Long–Range Restriction Map of the Human Chromosome 19q13 Region: Close Physical Linkage Between CKMM . . . ERCC2 Genes," *AM. J. HUM. GENET.* 46:492–501 (1990).

Johnson, K., et al., "A New Polymorphic Probe Which Defines the Region of Chromosome 19 Containing the Myotoic Dystrophy Locus," *AM. J. HUM. GENET.* 46:1073–1081 (1990).

Ropers, H.H., et al., "Report of the second international workshop on human chromosome 19 mapping," *Cytogenetics & Cell Genetics*:92–95 (1992).

Bowden, D.W., et al,, "Studies on locus expansion, library representation, and Chromosome walking using an efficient method to screen cosmid libraries," *Gene* 71:391–400 (1988).

Shaw, Duncan J., et al., "Genomic Organization and Transcriptional Units at the Myotonic Dystrophy Locus," *GENOMICS,* 18:673–679 (1993).

Hofmann–Radvanyi, Helene, et al., "Myotonic dystrophy: absence of CTG enlarged transcript in congenital forms, and low expression of the normal allele," *Hum. Mol. Genetics,* 2(8):1263–1266 (1993).

Wieringa, Bé, "Commentary: Myotonic dystrophy reviewed: back to the future?," *Hum. Mol. Genetics,* 3 (1):1–7 (1994).

Carango, Paul, et al., "Absence of Myotonic Dystrophy Protein Kinase 9DMPK) mRNA as a Result of a Triplet Repeat Expansion in Myotonic Dystrophy," GENOMICS, 18:340–348 (1993).

FIG. 1B

```
101
CTTCCCCAGGCCTGCAGTTTGCCCAATCCACGTCAGGGCCTCAGCCTGGCCGAAAGAAAGAAATG
GAAGGGTCCGGACGTCAAACGGGTTAGGTGCAGTCCCGGAGTCGGACCGGCTTTCTTTCTTTAC

GTCTTGTATCCCCCAGCAGCAGCAGCATTCCCGGCTACAAGGACCCTTCGAGCCCCGTTC
CAGAACATAGGGGGGTCGTCGTCGTAAGGGCCGATGTTCCTGGGAAGCTCGGGGCAAG
                                                            102
```

```
  1   CCCCCAGGACAAGTACGTGGCCGACTTCTTGCAGTGGGCGGAGCCATC
      P  P  G  Q  V  R  G  R  L  L  A  V  G  G  A  I

49   GTGGTGAGGCTTAAGGAGGTCCGACTGCAGAGGGACGACTTCGAGATT
      V  V  R  L  K  E  V  R  L  Q  R  D  D  F  E  I

97   CTGAAGGTGATCGGACGCGGGGCGTTCAGCGAGGTAGCGGTAGTGAAG
      L  K  V  I  G  R  G  A  F  S  E  V  A  V  V  K

145   ATGAAGCAGACGGGCCAGGTGTATGCCATGAAGATCATGAACAAGTGG
      M  K  Q  T  G  Q  V  Y  A  M  K  I  M  N  K  W

193   GACATGCTGAAGAGGGGCGAGGTGTCGTGCTTCCGTGAGGAGAGGGAC
      D  M  L  K  R  G  E  V  S  C  F  R  E  E  R  D

241   GTGTTGGTGAATGGGGACCGGCGGTGGATCACGCAGCTGCACTTCGCC
      V  L  V  N  G  D  R  R  W  I  T  Q  L  H  F  A

289   TTCCAGGATGAGAACTACCTGTACCTGGTCATGGAGTATTACGTGGGC
      F  Q  D  E  N  Y  L  Y  L  V  M  E  Y  Y  V  G

337   GGGGACCTGCTGACACTGCTGAGCAAGTTTGGGGAGCGGATTCCGGCC
      G  D  L  L  T  L  L  S  K  F  G  E  R  I  P  A

385   GAGATGGCGCGCTTCTACCTGGCGGAGATTGTCATGGCCATAGACTCG
      E  M  A  R  F  Y  L  A  E  I  V  M  A  I  D  S

433   GTGCACCGGCTTGGCTACGTGCACAGGGACATCAAACCCGACAACATC
      V  H  R  L  G  Y  V  H  R  D  I  K  P  D  N  I

481   CTGCTGGACCGCTGTGGCCACATCCGCCTGGCCGACTTCGGCTCTTGC
      L  L  D  R  C  G  H  I  R  L  A  D  F  G  S  C

529   CTCAAGCTGCGGGCAGATGGAACGGTGCGGTCGCTGGTGGCTGTGGGC
      L  K  L  R  A  D  G  T  V  R  S  L  V  A  V  G

577   ACCCCAGACTACCTGTCCCCCGAGATCCTGCAGGCTGTGGGCGGTGGG
      T  P  D  Y  L  S  P  E  I  L  Q  A  V  G  G  G

625   CCTGGGACAGGCAGCTACGGGCCCGAGTGTGACTGGTGGGCGCTGGGT
      P  G  T  G  S  Y  G  P  E  C  D  W  W  A  L  G

673   GTATTCGCCTATGAAATGTTCTATGGGCAGACGCCCTTCTACGCGGAT
      V  F  A  Y  E  M  F  Y  G  Q  T  P  F  Y  A  D
```

FIG. 5A

```
721   TCCACGGCGGAGACCTATGGCAAGATCGTCCACTACAAGGAGCACCTC
       S  T  A  E  T  Y  G  K  I  V  H  Y  K  E  H  L

769   TCTCTGCCGCTGGTGGACGAAGGGGTCCCTGAGGAGGCTCGAGACTTC
       S  L  P  L  V  D  E  G  V  P  E  E  A  R  D  F

817   ATTCAGCGGTTGCTGTGTCCCCCGGAGACACGGCTGGGCCGGGGTGGA
       I  Q  R  L  L  C  P  P  E  T  R  L  G  R  G  G

865   GCAGGCGACTTCCGGACACATCCCTTCTTCTTTGGCCTCGACTGGGAT
       A  G  D  F  R  T  H  P  F  F  F  G  L  D  W  D

913   GGTCTCCGGGACAGCGTGCCCCCCTTTACACCGGATTTCGAAGGTGCC
       G  L  R  D  S  V  P  P  F  T  P  D  F  E  G  A

961   ACCGACACATGCAACTTCGACTTGGTGGAGGACGGGCTCACTGCCATG
       T  D  T  C  N  F  D  L  V  E  D  G  L  T  A  M

1009  GAGACACTGTCGGACATTCGGGAAGGTGCGCCGCTAGGGGTCCACCTG
       E  T  L  S  D  I  R  E  G  A  P  L  G  V  H  L

1057  CCTTTTGTGGGCTACTCCTACTCCTGCATGGCCCTCAGGGACAGTGAG
       P  F  V  G  Y  S  Y  S  C  M  A  L  R  D  S  E

1105  GTCCCAGGCCCCACACCCATGGAAGTGGAGGCCGAGCAGCTGCTTGAG
       V  P  G  P  T  P  M  E  V  E  A  E  Q  L  L  E

1153  CCACACGTGCAAGCGCCCAGCCTGGAGCCCTCGGTGTCCCCACAGGAT
       P  H  V  Q  A  P  S  L  E  P  S  V  S  P  Q  D

1201  GAAACAGCTGAAGTGGCAGTTCCAGCGGCTGTCCCTGCGGCAGAGGCT
       E  T  A  E  V  A  V  P  A  A  V  P  A  A  E  A

1249  GAGGCCGAGGTGACGCTGCGGGAGCTCCAGGAAGCCCTGGAGGAGGAG
       E  A  E  V  T  L  R  E  L  Q  E  A  L  E  E  E

1297  GTGCTCACCCGGCAGAGCCTGAGCCGGGAGATGGAGGCCATCCGCACG
       V  L  T  R  Q  S  L  S  R  E  M  E  A  I  R  T

1345  GACAACCAGAACTTCGCCAGTCAACTACGCGAGGCAGAGGCTCGGAAC
       D  N  Q  N  F  A  S  Q  L  R  E  A  E  A  R  N

1393  CGGGACCTAGAGGCACACGTCCGGCAGTTGCAGGAGCGGATGGAGTTG
       R  D  L  E  A  H  V  R  Q  L  Q  E  R  M  E  L
```

FIG. 5B

```
1441    CTGCAGGCAGAGGGAGCCACAGCTGTCACGGGGGTCCCCAGTCCCCGG
        L  Q  A  E  G  A  T  A  V  T  G  V  P  S  P  R

1489    GCCACGGATCCACCTTCCCATCTAGATGGCCCCCCGGCGTGGCTGTGG
        A  T  D  P  P  S  H  L  D  G  P  P  A  W  L  W

1537    GCCAGTGCCCGCTGGTGGGGCCAGGCCATGCACCGCCGCCACCTGCTG
        A  S  A  R  W  W  G  Q  A  M  H  R  R  H  L  L

1585    CTCCCTGCCAGGGTCCCTAGGCCTGGCCTATCGGAGGCGCTTTCCCTG
        L  P  A  R  V  P  R  P  G  L  S  E  A  L  S  L

1633    CTCCTGTTCGCCGTTGTTCTGTCTCGTGCCGCCGCCCTGGGCTGCATT
        L  L  F  A  V  V  L  S  R  A  A  A  L  G  C  I

1681    GGGTTGGTGGCCCACGCCGGCCAACTCACCGCAGTCTGGCGCCGCCCA
        G  L  V  A  H  A  G  Q  L  T  A  V  W  R  R  P

1729    GGAGCCGCCCGCGCTCCCTGAACCCTAGAACTGTCTTCGACTCCGGGG
        G  A  A  R  A  P

1777    CCCCGTTGGAAGACTGAGTGCCCGGGGCCAGCACAGAAGCCGCGCCCA
1825    CCGCCTGCCAGTTCACAACCGCTCCGAGCGTGGGTCTCCGCCCAGCTC
1873    CAGTCCTGTGATCCGGGCCCGCCCCCTAGCGGCCGGGGAGGGAGGGGC
1921    CGGGTCCGCGGCCGGCGAACGGGGCTCGAAGGGTCCTTGTAGCCGGGA
1969    ATGCTGCTGCTGCTGCTGCTGCTGCTGCTGCTGGGGGGATCACAG
2017    ACCATTTCTTTCTTTCGGCCAGGCTGAGGCCCTGACGTGGATGGGCAA
2065    ACTGCAGGCCTGGGAAGGCAGCAAGCCGGGCCGTCCGTGTTCCATCCT
2113    CCACGCACCCCCACCTATCGTTGGTTCGCAAAGTGCAAAGCTTTCTTG
2161    TGCATGACGCCCTGCTCTGGGGAGCGTCTGGCGCGATCTCTGCCTGCT
2209    TACTCGGGAAATTTGCTTTTGCCAAACCCGCTTTTTCGGGGATCCCGC
2257    GCCCCCCTCCTCACTTGCGCTGCTCTCGGAGCCCCAGCCGGCTCCGCC
2305    GCCTTCGGCGGTTTGGATATTTATTGACCTCGTCCTCCGACTCGCTGA
2353    CAGGCTACAGGACCCCCAACAACCCCAATCCACGTTTTGGATGCACTG
2401    AGACCCCGACATTCCTCGGTATTTATTGTCTGTCCCCACCTAGGACCC
2449    CCACCCCCGACCCTCGCGAATAAAAGGCCCTCCATCTGCCCAAAAAAA
2497    AAAAAAAAAAAAAAA
```

FIG. 5C

```
         aaaaaaaaaaaaGCTGGTATAAAGCAGAGAGCCTGAGGGCTAAATTTAACTGTCCGAGTC
  1      ---------+---------+---------+---------+---------+---------+    60
         tttttttttttttCGACCATATTTCGTCTCTCGGACTCCCGATTTAAATTGACAGGCTCAG GGAATCCATCTCTGAGTCACCCAAGAAGCTGCCCTGGCCTCCCGTCCCCTTCCCAGGCCT
  61     ---------+---------+---------+---------+---------+---------+    120
         CCTTAGGTAGAGACTCAGTGGGTTCTTCGACGGGACCGGAGGGCAGGGGAAGGGTCCGGA CAACCCCTTTCTCCCACCCAGCCCCAACCCCCAGCCCTCACCCCCTAGCCCCCAGTTCTG
  121    ---------+---------+---------+---------+---------+---------+    180
         GTTGGGGAAAGAGGGTGGGTCGGGGTTGGGGGTCGGGAGTGGGGGATCGGGGGTCAAGAC GAGCTTGTCGGGAGCAAGGGGGTGGTTGCTACTGGGTCACTCAGCCTCAATTGGCCCTGT
  181    ---------+---------+---------+---------+---------+---------+    240
         CTCGAACAGCCCTCGTTCCCCCACCAACGATGACCCAGTGAGTCGGAGTTAACCGGGACA TTCAGCAATGGGCAGGTTCTTCTTGAAATTCATCACACCTGTGGCTTCCTCTGTGCTCTA
  241    ---------+---------+---------+---------+---------+---------+    300
         AAGTCGTTACCCGTCCAAGAAGAACTTTAAGTAGTGTGGACACCGAAGGAGACACGAGAT CCTTTTTATTGGGGTGACAGTGTGACAGCTGAGATTCTCCATGCATTCCCCCTACTCTAG
  301    ---------+---------+---------+---------+---------+---------+    360
         GGAAAAATAACCCCACTGTCACACTGTCGACTCTAAGAGGTACGTAAGGGGGATGAGATC CACTGAAGGGTTCTGAAGGGCCCTGGAAGGAGGGAGCTTGGGGGGCTGGCTTGTGAGGGG
  361    ---------+---------+---------+---------+---------+---------+    420
         GTGACTTCCCAAGACTTCCCGGGACCTTCCTCCCTCGAACCCCCCGACCGAACACTCCCC TTAAGGCTGGGAGGCGGGAGGGGGGCTGGACCAAGGGGTGGGGAGAAGGGGAGGAGGCCT
  421    ---------+---------+---------+---------+---------+---------+    480
         AATTCCGACCCTCCGCCCTCCCCCCGACCTGGTTCCCCACCCCTCTTCCCCTCCTCCGGA
```

FIG. 6A

```
                    genomic sequence ← | → cDNA 41
      CGGCCGGCCGCAGAGAGAAGTGGCCAGAGAGGCCCAGGGGACAGCCAGGGACAGGCAGA
481   ---------+---------+---------+--------+---------+---------+   540
      GCCGGCCGGCGTCTCTCTTCACCGGTCTCTCCGGGTCCCCTGTCGGTCCCTGTCCGTCT CATGCAGCCAGGGCTCCAGGGCCTGGACAGGGGCTGCCAGGCCCTGTGACAGGAGGACCC
541   ---------+---------+---------+---------+---------+---------+   600
      GTACGTCGGTCCCGAGGTCCCGGACCTGTCCCCGACGGTCCGGGACACTGTCCTCCTGGG CGAGCCCCCGGCCCGGGGAGGGGCCATGGTGCTGCCTGTCCAACATGTCAGCCGAGGTGC
601   ---------+---------+---------+---------+---------+---------+   660
      GCTCGGGGGCCGGGCCCCTCCCCGGTACCACGACGGACAGGTTGTACAGTCGGCTCCACG

M   S   A   E   V   R

GGCTGAGGCGGCTCCAGCAGCTGGTGTTGGACCCGGGCTTCCTGGGGCTGGAGCCCCTGC
661   ---------+---------+---------+---------+---------+---------+   720
      CCGACTCCGCCGAGGTCGTCGACCACAACCTGGGCCCGAAGGACCCCGACCTCGGGGACG

L   R   R   L   Q   Q   L   V   L   D   P   G   F   L   G   L   E   P   L   L

| → cDNA28
      TCGACCTTCTCCTGGGCGTCCACCAGGAGCTGGGCGCCTCCGAACTGGCCCAGGACAAGT
721   ---------+---------+---------+---------+--------+---------+   780
      AGCTGGAAGAGGACCCGCAGGTGGTCCTCGACCCGCGGAGGCTTGACCGGGTCCTGTTCA

D   L   L   G   V   H   Q   E   L   G   A   S   E   L   A   Q   D   K   Y

ACGTGGCCGACTTCTTGCAGXXXTGGGCGGAGCCCATCGTGGTGAGGCTTAAGGAGGTCC
781   ---------+---------+---------+---------+---------+---------+   840
      TGCACCGGCTGAAGAACGTCXXXACCCGCCTCGGGTAGCACCACTCCGAATTCCTCCAGG

```
841  GACTGCAGAGGGACGACTTCGAGATTCTGAAGGTGATCGGACGCGGGGCGTTCAGCGXXX  900
     ---------+---------+---------+---------+---------+---------+
     CTGACGTCTCCCTGCTGAAGCTCTAAGACTTCCACTAGCCTGCGCCCCGCAAGTCGCXXX

L  Q  R  D  D  F  E  I  L  K  V  I  G  R  G  A  F  S  X  X

901  AGGTAGCGGTAGTGAAGATGAAGCAGACGGGCCAGGTGTATGCCATGAAGATCATGAACA  960
     ---------+---------+---------+---------+---------+---------+
     TCCATCGCCATCACTTCTACTTCGTCTGCCCGGTCCACATACGGTACTTCTAGTACTTGT

V  A  V  V  K  M  K  Q  T  G  Q  V  Y  A  M  L  I  M  N  K

961  AGTGGGACATGCTGAAGAGGGGCGAGXXXGTGTCGTGCTTCCGTGAGGAGAGGGACGTGT  1020
     ---------+---------+---------+---------+---------+---------+
     TCACCCTGTACGACTTCTCCCCGCTCXXXCACAGCACGAAGGCACTCCTCTCCCTGCACA

W  D  M  L  K  R  G  E  X  V  S  C  F  R  E  E  R  D  V  L

1021 TGGTGAATGGGGACCGGCGGTGGATCACGCAGCTGCACTTCGCCTTCCAGGATGAGAACT  1080
     ---------+---------+---------+---------+---------+---------+
     ACCACTTACCCCTGGCCGCCACCTAGTGCGTCGACGTGAAGCGGAAGGTCCTACTCTTGA

V  N  G  D  R  R  W  I  T  Q  L  H  F  A  F  Q  D  E  N  Y

1081 ACCTGXXXTACCTGGTCATGGAGTATTACGTGGGCGGGGACCTGCTGACACTGCTGAGCA  1140
     ---------+---------+---------+---------+---------+---------+
     TGGACXXXATGGACCAGTACCTCATAATGCACCCGCCCCTGGACGACTGTGACGACTCGT

```
         AGTTTGGGGAGCGGATTCCGGCCGAGATGGCGCGCTTCTACCTGGCGGAGATTGTCATGG
1141     ---------+---------+---------+---------+---------+---------+    1200
         TCAAACCCCTCGCCTAAGGCCGGCTCTACCGCGCGAAGATGGACCGCCTCTAACAGTACC

F  G  E  R  I  P  A  E  M  A  R  F  Y  L  A  E  I  V  M  A

CCATAGACTCGGTGCACCGGCTTGGCTACGTGCACAGXXXGGACATCAAACCCGACAACA
1201     ---------+---------+---------+---------+---------+---------+    1260
         GGTATCTGAGCCACGTGGCCGAACCGATGCACGTGTCXXXCCTGTAGTTTGGGCTGTTGT

I  D  S  V  H  R  L  G  Y  V  H  X  X  D  I  K  P  D  N  L

TCCTGCTGGACCGCTGTGGCCACATCCGCCTGGCCGACTTCGGCTCTTGCCTCAAGCTGC
1261     ---------+---------+---------+---------+---------+---------+    1320
         AGGACGACCTGGCGACACCGGTGTAGGCGGACCGGCTGAAGCCGAGAACGGAGTTCGACG

L  L  D  R  C  G  H  I  R  L  A  D  F  G  S  C  L  K  L  R

GGGCAGATGGAACGXXXGTGCGGTCGCTGGTGGCTGTGGGCACCCCAGACTACCTGTCCC
1321     ---------+---------+---------+---------+---------+---------+    1380
         CCCGTCTACCTTGCXXXCACGCCAGCGACCACCGACACCCGTGGGGTCTGATGGACAGGG

A  D  G  T  X  V  R  S  L  V  A  V  G  T  P  D  Y  L  S  P

CCGAGATCCTGCAGGCTGTGGGCGGTGGGCCTGGGACAGGCAGCTACGGGCCCGAGTGTG
1381     ---------+---------+---------+---------+---------+---------+    1440
         GGCTCTAGGACGTCCGACACCCGCCACCCGGACCCTGTCCGTCGATGCCCGGGCTCACAC

```
1141   ACTGGTGGGCGCTGGGTGTATTCGCCTATGAAATGTTCTATGGGCAGACGCCCTTCTACG
       ---------+---------+---------+---------+---------+---------+   1500
       TGACCACCCGCGACCCACATAAGCGGATACTTTACAAGATACCCGTCTGCGGGAAGATGC

W  W  A  L  G  V  F  A  Y  E  M  F  Y  G  Q  T  P  F  Y  A

1501   CGGATTCCACGGCGGAGACCTATGGCAAGATCGTCCACTAXXXCAAGGAGCACCTCTCTC
       ---------+---------+---------+---------+---------+---------+   1560
       GCCTAAGGTGCCGCCTCTGGATACCGTTCTAGCAGGTGATXXXGTTCCTCGTGGAGAGAG

D  S  T  A  E  T  Y  G  K  I  V  H  X  X  K  E  H  L  S  L

1561   TGCCGCTGGTGGACGAAGGGGTCCCTGAGGAGGCTCGAGACTTCATTCAGCGGTTGCTGT
       ---------+---------+---------+---------+---------+---------+   1620
       ACGGCGACCACCTGCTTCCCCAGGGACTCCTCCGAGCTCTGAAGTAAGTCGCCAACGACA

P  L  V  D  E  G  V  P  E  E  A  R  D  F  I  Q  R  L  L  C

1621   GTCCCCCGGAGACACGGCTGGGCCGGGGTGGAGCAGGCGACTTCCGGACACATCCCTTCT
       ---------+---------+---------+---------+---------+---------+   1680
       CAGGGGGCCTCTGTGCCGACCCGGCCCCACCTCGTCCGCTGAAGGCCTGTGTAGGGAAGA

P  P  E  T  R  L  G  R  G  G  A  G  D  F  R  T  H  P  F  F

1681   TCTTTGGCCTCGACTGGGATGGTCTCCGGGACAGCGTGCCCCCCTTTACACCGGATTTCG
       ---------+---------+---------+---------+---------+---------+   1740
       AGAAACCGGAGCTGACCCTACCAGAGGCCCTGTCGCACGGGGGGAAATGTGGCCTAAAGC

```
           AAGGTGCCACCGACACATGCAACTTCGACTTGGTGGAGAACGGGCTCACTGCCATGXXXG
  1741     ---------+---------+---------+---------+---------+---------+     1800
           TTCCACGGTGGCTGTGTACGTTGAAGCTGAACCACCTCCTGCCCGAGTGACGGTACXXXC

G  A  T  D  T  C  N  F  D  L  V  E  D  G  L  T  A  M  X  E

AGACACTGTCGGACATTCGGGAAGGTGCGCCGCTAGGGGTCCACCTGCCTTTTGTGGGCT
  1801     ---------+---------+---------+---------+---------+---------+     1860
           TCTGTGACAGCCTGTAAGCCCTTCCACGCGGCGATCCCCAGGTGGACGGAAAACACCCGA

T  L  S  D  I  R  E  G  A  P  L  G  V  H  L  P  F  V  G  Y

ACTCCTACTCCTGCATGGCCCTCAGXXXGGACAGTGAGGTCCCAGGCCCCACACCCATGG
  1861     ---------+---------+---------+---------+---------+---------+     1920
           TGAGGATGAGGACGTACCGGGAGTCXXXCCTGTCACTCCAGGGTCCGGGGTGTGGGTACC

S  Y  S  C  M  A  L  X  X  D  S  E  V  P  G  P  T  P  M  E

AAGTGGAGGCCGAGCAGCTGCTTGAGCCACACGTGCAAGCGCCCAGCCTGGAGCCCTCGG
  1921     ---------+---------+---------+---------+---------+---------+     1980
           TTCACCTCCGGCTCGTCGACGAACTCGGTGTGCACGTTCGCGGGTCGGACCTCGGGAGCC

V  E  A  E  Q  L  L  E  P  H  V  Q  A  P  S  L  E  P  S  V

TGTCCCCACAGGATGAAACAXXXGCTGAAGTGGCAGTTCCAGCGGCTGTCCCTGCGGCAG
  1981     ---------+---------+---------+---------+---------+---------+     2040
           ACAGGGGTGTCCTACTTTGTXXXCGACTTCACCGTCAAGGTCGCCGACAGGGACGCCGTC

```
                AGGCTGAGGCCGAGGTGACGCTGCGGGAGCTCCAGGAAGCCCTGGAGGAGGAGGTGCTCA
   2041         ---------+---------+---------+---------+---------+---------+   2100
                TCCGACTCCGGCTCCACTGCGACGCCCTCGAGGTCCTTCGGGACCTCCTCCTCCACGAGT

A   E   A   E   V   T   L   R   E   L   Q   E   A   L   E   E   E   V   L   T

CCCGGCAGAGCCTGAGCCGGGAGATGGAGGCCATCCGCACGGACAACCAGAACTTCGCCA
   2101         ---------+---------+---------+---------+---------+---------+   2160
                GGGCCGTCTCGGACTCGGCCCTCTACCTCCGGTAGGCGTGCCTGTTGGTCTTGAAGCGGT

R   Q   S   L   S   R   E   M   E   A   I   R   T   D   N   Q   N   F   A   X

GXXXTCAACTACGCGAGGCAGAGGCTCGGAACCGGGACCTAGAGGCACACGTCCGGCAGT
   2161         ---------+---------+---------+---------+---------+---------+   2220
                CXXXAGTTGATGCGCTCCGTCTCCGAGCCTTGGCCCTGGATCTCCGTGTGCAGGCCGTCA

X   Q   L   R   E   A   E   A   R   N   R   D   L   E   A   H   V   R   Q   L

TGCAGGAGCGGATGGAGTTGCTGCAGGCAGAGGGAGCCACAGXXXCTGTCACGGGGGTCC
   2221         ---------+---------+---------+---------+---------+---------+   2280
                ACGTCCTCGCCTACCTCAACGACGTCCGTCTCCCTCGGTGTCXXXGACAGTGCCCCCAGG

Q   E   R   M   E   L   L   Q   A   E   G   A   T   X   X   V   T   G   V   P

CCAGTCCCCGGGCCACGGATCCACCTTCCCATXXXCTAGATGGCCCCCCGGCCGTGGCTG
   2281         ---------+---------+---------+---------+---------+---------+   2340
                GGTCAGGGGCCCGGTGCCTAGGTGGAAGGGTAXXXGATCTACCGGGGGGCCGGCACCGAC

```
2341  TGGGCCAGTGCCCGCTGGTGGGGCCAGGCCCCATGCACCGCCGCCACCTGCTGCTCCCTG  2400
      ---------+---------+---------+---------+---------+---------+
      ACCCGGTCACGGGCGACCACCCCGGTCCGGGGTACGTGCCGGCGGTGGACGACGAGGGAC

G  Q  C  P  L  V  G  P  G  P  M  H  R  R  H  L  L  P  A

2401  CCAGGXXXGTCCCTAGGCCTGGCCTATCGGAGGCGCTTTCCCTGCTCCTGTTCGCCGTTG  2460
      ---------+---------+---------+---------+---------+---------+
      GGTCCXXXCAGGGATCCGGACCGGATAGCCTCCGCGAAAGGGACGAGGACAAGCGGCAAC

R  X  V  P  R  P  G  L  S  E  A  L  S  L  L  F  A  V  V

2461  TTCTGTCTCGTGCCGCCGCCCTGGGCTGCATTGGGTTGGTGGCCCACGCCGGCCAACTCA  2520
      ---------+---------+---------+---------+---------+---------+
      AAGACAGAGCACGGCGGCGGGACCCGACGTAACCCAACCACCGGGTGCGGCCGGTTGACT

L  S  R  A  A  A  L  G  C  I  G  L  V  A  H  A  G  Q  L  T

2521  CCGCAGTCTGGCGCCGCCCAGGAGCCGCCCGCGCTCCCTGAACCCTAGAACTGTCTTCGA  2580
      ---------+---------+---------+---------+---------+---------+
      GGCGTCAGACCGCGGCGGGTCCTCGGCGGGCGCGAGGGACTTGGGATCTTGACAGAAGCT

A  V  W  R  R  P  G  A  A  R  A  P

2581  CTCCGGGGCCCCGTTGGAAGACTGAGTGCCCGGGGCCAGCACAGAAGCCGCGCCCACCGC  2640
      ---------+---------+---------+---------+---------+---------+
      GAGGCCCCGGGGCAACCTTCTGACTCACGGGCCCCGGTCGTGTCTTCGGCGCGGGTGGCG

2641  CTGCCAGTTCACAACCGCTCCGAGCGTGGGTCTCCGCCCAGCTCCAGTCCTGTGATCCGG  2700
      ---------+---------+---------+---------+---------+---------+
      GACGGTCAAGTGTTGGCGAGGCTCGCACCCAGAGGCGGGTCGAGGTCAGGACACTAGGCC
```

FIG. 6H

```
        GCCCGCCCCCTAGCGGCCGGGGAGGGAGGGGCCGGGTCCGCGGCCGGCGAACGGGGCTCG
2701    ---------+---------+---------+---------+---------+---------+    2760
        CGGGCGGGGGATCGCCGGCCCCTCCCTCCCCGGCCCAGGCGCCGGCCGCTTGCCCCGAGC

AAGGGTCCTTGTAGCCGGGAATGCTGCTGCTGCTGCTGCTGCTGCTGCTGCTGCTGGGGG
2761    ---------+---------+---------+---------+---------+---------+    2820
        TTCCCAGGAACATCGGCCCTTACGACGACGACGACGACGACGACGACGACGACGACCCCC

CATCACAGACCATTTCTTTCTTTCGGCCAGGCTGAGGCCCTGACGTGGATGGGCAAACTG
2821    ---------+---------+---------+---------+---------+---------+    2880
        CTAGTGTCTGGTAAAGAAAGAAAGCCGGTCCGACTCCGGGACTGCACCTACCCGTTTGAC

CAGGCCTGGGAAGGCAGCAAGCCGGGCCGTCCGTGTTCCATCCTCCACGCACCCCCACCT
2881    ---------+---------+---------+---------+---------+---------+    2940
        GTCCGGACCCTTCCGTCGTTCGGCCCGGCAGGCACAAGGTAGGAGGTGCGTGGGGTGGA

ATCGTTGGTTCGCAAAGTGCAAAGCTTTCTTGTGCATGACGCCCTGCTCTGGGGAGCGTC
2941    ---------+---------+---------+---------+---------+---------+    3000
        TAGCAACCAAGCGTTTCACGTTTCGAAAGAACACGTACTGCGGGACGAGACCCCTCGCAG

TGGCGCGATCTCTGCCTGGTTACTCGGGAAATTTGCTTTTGCCAAACCCGCTTTTTCGGG
3001    ---------+---------+---------+---------+---------+---------+    3060
        ACCGCGCTAGAGACGGACGAATGAGCCCTTTAAACGAAAACGGTTTGGGCGAAAAAGCCC

GATCCCGCGCCCCCCTCCTCACTTGCGCTGCTCTCGGAGCCCCAGCCGGCTCCGCCGCCT
3061    ---------+---------+---------+---------+---------+---------+    3120
        CTAGGGCGCGGGGGGAGGAGTGAACGCGACGAGAGCCTCGGGGTCGGCCGAGGCGGCGGA

TCGGCGGTTTGGATATTTATTGACCTCGTCCTCCGACTCGCTGACAGGCTACAGGACCCC
3121    ---------+---------+---------+---------+---------+---------+    3180
        AGCCGCCAAACCTATAAATAACTGGAGCAGGAGGCTGAGCGACTGTCCGATGTCCTGGGG

CAACAACCCCAATCCACGTTTTGGATGCACTGAGACCCCGACATTCCTCGGTATTTATTG
3181    ---------+---------+---------+---------+---------+---------+    3240
        GTTGTTGGGGTTAGGTGCAAAACCTACGTGACTCTGGGGCTGTAAGGAGCCATAAATAAC
```

FIG. 6I

```
      TCTGTCCCCACCTAGGACCCCCACCCCCGACCCTCGCGAATAAAAGGCCCTCCATCTGCC
3241  ---------+---------+---------+---------+---------+---------+  3300
      AGACAGGGGTGGATCCTGGGGGTGGGGGCTGGGAGCGCTTATTTTCCGGGAGGTAGACGG

CAAAAAAAAAAAAAAAAAAAAAA
3301  ---------+---------+---   3323
      GTTTTTTTTTTTTTTTTTTTTTT
```

FIG. 6J

| | | | | | | |
|---|---|---|---|---|---|---|
| GGGGACAGCC | AGGGACAGGC | AGACATGCAG | CCAGGGCTCC | AGGGCCTGGA | CAGGGGCTGC | 60 |
| CAGGCCCTGT | GACAGGAGGA | CCCCGAGCCC | CCGGCCCGGG | GAGGGGCCAT | GGTGCTGCCT | 120 |
| GTCCAACATG | TCAGCCGAGG | TGCGGCTGAG | GCGGCTCCAG | CAGCTGGTGT | GGACCCGGG | 180 |
| CTTCCTGGGG | CTGGAGCCCC | TGCTCGACCT | TCTCCTGGGC | GTCCACCAGG | AGCTGGGCGC | 240 |
| CTCCGAACTG | GCCCAGGACA | AGTACGTGGC | CGACTTCTTG | CAGTGGGCGG | AGCCCATCGT | 300 |
| GGTGAGGCTT | AAGGAGGTCC | GACTGCAGAG | GGACGACTTC | GAGATTCTGA | AGGTGATCGG | 360 |
| ACGCGGGGCG | TTCAGCGAGG | TAGCGGTAGT | GAAGATGAAG | CAGACGGGCC | AGGTGTATGC | 420 |
| CATGAAGATC | ATGAACAAGT | GGGACATGCT | GAAGAGGGGC | GAGGTGTCGT | GCTTCCGTGA | 480 |
| GGAGAGGGAC | GTGTTGGTGA | ATGGGACCG | GCGGTGGATC | ACGCAGCTGC | ACTTCGCCTT | 540 |
| CCAGGATGAG | AACTACCTGT | ACCTGGTCAT | GGAGTATTAC | GTGGGCGGGG | ACCTGCTGAC | 600 |
| ACTGCTGAGC | AAGTTTGGGG | AGCGGATTCC | GGCCGAGATG | GCGCGCTTCT | ACCTGGCGGA | 660 |
| GATTGTCATG | GCCATAGACT | CGGTGCACCG | GCTTGGCTAC | GTGCACAGGG | ACATCAAACC | 720 |
| CGACAACATC | CTGCTGGACC | GCTGTGGCCA | CATCCGCCTG | GCCGACTTCG | GCTCTTGCCT | 780 |
| CAAGCTGCGG | GCAGATGGAA | CGGTGCGGTC | GCTGGTGGCT | GTGGGCACCC | CAGACTACCT | 840 |
| GTCCCCCGAG | ATCCTGCAGG | CTGTGGGCGG | TGGGCCTGGG | ACAGGCAGCT | ACGGGCCCGA | 900 |
| GTGTGACTGG | TGGGCGCTGG | GTGTATTCGC | CTATGAAATG | TTCTATGGGC | AGACGCCCTT | 960 |
| CTACGCGGAT | TCCACGGCGG | AGACCTATGG | CAAGATCGTC | CACTACAAGG | AGCACCTCTC | 1020 |
| TCTGCCGCTG | GTGGACGAAG | GGGTCCCTGA | GGAGGCTCGA | GACTTCATTC | AGCGGTTGCT | 1080 |
| GTGTCCCCCG | GAGACACGGC | TGGGCCGGGG | TGGAGCAGGC | GACTTCCGGA | CACATCCCTT | 1140 |
| CTTCTTTGGC | CTCGACTGGG | ATGGTCTCCG | GGACAGCGTG | CCCCCCTTTA | CACCGGATTT | 1200 |
| CGAAGGTGCC | ACCGACACAT | GCAACTTCGA | CTTGGTGGAG | GACGGGCTCA | CTGCCATGGA | 1260 |
| GACACTGTCG | GACATTCGGG | AAGGTGCGCC | GCTAGGGGTC | CACCTGCCTT | TTGTGGGCTA | 1320 |
| CTCCTACTCC | TGCATGGCCC | TCAGGGACAG | TGAGGTCCCA | GGCCCACAC | CCATGGAAGT | 1380 |
| GGAGGCCGAG | CAGCTGCTTG | AGCCACACGT | GCAAGCGCCC | AGCCTGGAGC | CCTCGGTGTC | 1440 |
| CCCACAGGAT | GAAACAGCTG | AAGTGGCAGT | TCCAGCGGCT | GTCCCTGCGG | CAGAGGCTGA | 1500 |

FIG. 8A

```
GGCCGAGGTG ACGCTGCGGG AGCTCCAGGA AGCCCTGGAG GAGGAGGTGC TCACCCGGCA    1560

GAGCCTGAGC CGGGAGATGG AGGCCATCCG CACGGACAAC CAGAACTTCG CCAGTCAACT    1620

ACGCGAGGCA GAGGCTCGGA ACCGGGACCT AGAGGCACAC GTCCGGCAGT TGCAGGAGCG    1680

GATGGAGTTG CTGCAGGCAG AGGGAGCCAC AGCTGTCACG GGGGTCCCCA GTCCCCGGGC    1740

CACGGATCCA CCTTCCCATC TAGATGGCCC CCCGGCCGTG GCTGTGGGCC AGTGCCCGCT    1800

GGTGGGGCCA GGCCCCATGC ACCGCCGCCA CCTGCTGCTC CCTGCCAGGG TCCCTAGGCC    1860

TGGCCTATCG GAGGCGCTTT CCCTGCTCCT GTTCGCCGTT GTTCTGTCTC GTGCCGCCGC    1920

CCTGGGCTGC ATTGGGTTGG TGGCCCACGC CGGCCAACTC ACCGCAGTCT GGCGCCGCCC    1980

AGGAGCCGCC CGCGCTCCCT GAACCCTAGA ACTGTCTTCG ACTCCGGGGC CCCGTTGGAA    2040

GACTGAGTGC CCGGGGCCAG CACAGAAGCC GCGCCCACCG CCTGCCAGTT CACAACCGCT    2100

CCGAGCGTGG GTCTCCGCCC AGCTCCAGTC CTGTGATCCG GGCCCGCCCC CTAGCGGCCG    2160

GGGAGGGAGG GGCCGGGTCC GCGGCCGGCG AACGGGGCTC GAAGGGTCCT TGTAGCCGGG    2220

AATGCTGCTG CTGCTGCTGC TGCTGCTGCT GCTGCTGGGG GGATCACAGA CCATTTCTTT    2280

CTTTCGGCCA GGCTGAGGCC CTGACGTGGA TGGGCAAACT GCAGGCCTGG GAAGGCAGCA    2340

AGCCGGGCCG TCCGTGTTCC ATCCTCCACG CACCCCCACC TATCGTTGGT TCGCAAAGTG    2400

CAAAGCTTTC TTGTGCATGA CGCCCTGCTC TGGGGAGCGT CTGGCGCGAT CTCTGCCTGC    2460

TTACTCGGGA AATTTGCTTT TGCCAAACCC GCTTTTTCGG GGATCCCGCG CCCCCCTCCT    2520

CACTTGCGCT GCTCTCGGAG CCCCAGCCGG CTCCGCCGCC TTCGGCGGTT TGGATATTTA    2580

TTGACCTCGT CCTCCGACTC GCTGACAGGC TACAGGACCC CCAACAACCC CAATCCACGT    2640

TTTGGATGCA CTGAGACCCC GACATTCCTC GGTATTTATT GTCTGTCCCC ACCTAGGACC    2700

CCCACCCCCG ACCCTCGCGA ATAAAA                                        2726
```

FIG. 8B

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

GGTGCGTGGA GGATGGAACA CGGAC    25

(2) INFORMATION FOR SEQ ID NO:2:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

GCGTGCGAGT GGACTAACAA CAGCTG    26

(2) INFORMATION FOR SEQ ID NO:3:

(i) SEQUENCE CHARACTERISTICS:
      (A) LENGTH: 25 base pairs
      (B) TYPE: nucleic acid
      (C) STRANDEDNESS: single (D) TOPOLOGY: linear (ii) MOLECULE TYPE: DNA (genomic)

(xi) SEQUENCE DESCRIPTION: SEQ ID NO:3:

CACGCTCGGA GCGGTTGTGA ACTGG                                          25

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CTTCCCAGGC CTGCAGTTTG CCCATC                                         26

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GAACGGGGCT CGAAGGGTCC TTGTAGC                                        27

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CCAGTTCACA ACCGCTCCGA GCGTG                                          25

(2) INFORMATION FOR SEQ ID NO:7:

(i) SEQUENCE CHARACTERISTICS:
        (A) LENGTH: 127 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:7:

CTTCCCAGGC CTGCAGTTTG CCCATCCACG TCAGGGCCTC AGCCTGGCCG AAAGAAAGAA     60

ATGGTCTTGT ATCCCCCCAG CAGCAGCAGC AGCATTCCCG GCTACAAGGA CCCTTCGAGC    120

CCCGTTC                                                              127

(2) INFORMATION FOR SEQ ID NO:8:

(i) SEQUENCE CHARACTERISTICS:
        (A) LENGTH: 2511 base pairs
        (B) TYPE: nucleic acid
        (C) STRANDEDNESS: double
        (D) TOPOLOGY: linear (ii) MOLECULE TYPE: DNA (genomic)

(ix) FEATURE:
    (A) NAME/KEY: CDS
    (B) LOCATION: 1..1746

(xi) SEQUENCE DESCRIPTION: SEQ ID NO:8:

```
CCC CCA GGA CAA GTA CGT GGC CGA CTT CTT GCA GTG GGC GGA GCC ATC      48
Pro Pro Gly Gln Val Arg Gly Arg Leu Leu Ala Val Gly Gly Ala Ile
 1               5                  10                  15

GTG GTG AGG CTT AAG GAG GTC CGA CTG CAG AGG GAC GAC TTC GAG ATT      96
Val Val Arg Leu Lys Glu Val Arg Leu Gln Arg Asp Asp Phe Glu Ile
            20                  25                  30

CTG AAG GTG ATC GGA CGC GGG GCG TTC AGC GAG GTA GCG GTA GTG AAG     144
Leu Lys Val Ile Gly Arg Gly Ala Phe Ser Glu Val Ala Val Val Lys
        35                  40                  45

ATG AAG CAG ACG GGC CAG GTG TAT GCC ATG AAG ATC ATG AAC AAG TGG     192
Met Lys Gln Thr Gly Gln Val Tyr Ala Met Lys Ile Met Asn Lys Trp
 50                  55                  60

GAC ATG CTG AAG AGG GGC GAG GTG TCG TGC TTC CGT GAG GAG AGG GAC     240
Asp Met Leu Lys Arg Gly Glu Val Ser Cys Phe Arg Glu Glu Arg Asp
 65                  70                  75                  80

GTG TTG GTG AAT GGG GAC CGG CGG TGG ATC ACG CAG CTG CAC TTC GCC     288
Val Leu Val Asn Gly Asp Arg Arg Trp Ile Thr Gln Leu His Phe Ala
                85                  90                  95

TTC CAG GAT GAG AAC TAC CTG TAC CTG GTC ATG GAG TAT TAC GTG GGC     336
Phe Gln Asp Glu Asn Tyr Leu Tyr Leu Val Met Glu Tyr Tyr Val Gly
            100                 105                 110

GGG GAC CTG CTG ACA CTG CTG AGC AAG TTT GGG GAG CGG ATT CCG GCC     384
Gly Asp Leu Leu Thr Leu Leu Ser Lys Phe Gly Glu Arg Ile Pro Ala
        115                 120                 125

GAG ATG GCG CGC TTC TAC CTG GCG GAG ATT GTC ATG GCC ATA GAC TCG     432
Glu Met Ala Arg Phe Tyr Leu Ala Glu Ile Val Met Ala Ile Asp Ser
130                 135                 140

GTG CAC CGG CTT GGC TAC GTG CAC AGG GAC ATC AAA CCC GAC AAC ATC     480
Val His Arg Leu Gly Tyr Val His Arg Asp Ile Lys Pro Asp Asn Ile
145                 150                 155                 160

CTG CTG GAC CGC TGT GGC CAC ATC CGC CTG GCC GAC TTC GGC TCT TGC     528
Leu Leu Asp Arg Cys Gly His Ile Arg Leu Ala Asp Phe Gly Ser Cys
                165                 170                 175

CTC AAG CTG CGG GCA GAT GGA ACG GTG CGG TCG CTG GTG GCT GTG GGC     576
Leu Lys Leu Arg Ala Asp Gly Thr Val Arg Ser Leu Val Ala Val Gly
            180                 185                 190

ACC CCA GAC TAC CTG TCC CCC GAG ATC CTG CAG GCT GTG GGC GGT GGG     624
Thr Pro Asp Tyr Leu Ser Pro Glu Ile Leu Gln Ala Val Gly Gly Gly
        195                 200                 205

CCT GGG ACA GGC AGC TAC GGG CCC GAG TGT GAC TGG TGG GCG CTG GGT     672
Pro Gly Thr Gly Ser Tyr Gly Pro Glu Cys Asp Trp Trp Ala Leu Gly
210                 215                 220

GTA TTC GCC TAT GAA ATG TTC TAT GGG CAG ACG CCC TTC TAC GCG GAT     720
Val Phe Ala Tyr Glu Met Phe Tyr Gly Gln Thr Pro Phe Tyr Ala Asp
225                 230                 235                 240

TCC ACG GCG GAG ACC TAT GGC AAG ATC GTC CAC TAC AAG GAG CAC CTC     768
Ser Thr Ala Glu Thr Tyr Gly Lys Ile Val His Tyr Lys Glu His Leu
                245                 250                 255

TCT CTG CCG CTG GTG GAC GAA GGG GTC CCT GAG GAG GCT CGA GAC TTC     816
Ser Leu Pro Leu Val Asp Glu Gly Val Pro Glu Glu Ala Arg Asp Phe
            260                 265                 270

ATT CAG CGG TTG CTG TGT CCC CCG GAG ACA CGG CTG GGC CGG GGT GGA     864
Ile Gln Arg Leu Leu Cys Pro Pro Glu Thr Arg Leu Gly Arg Gly Gly
        275                 280                 285
```

```
GCA GGC GAC TTC CGG ACA CAT CCC TTC TTC TTT GGC CTC GAC TGG GAT      912
Ala Gly Asp Phe Arg Thr His Pro Phe Phe Phe Gly Leu Asp Trp Asp
    290                 295                 300

GGT CTC CGG GAC AGC GTG CCC CCC TTT ACA CCG GAT TTC GAA GGT GCC      960
Gly Leu Arg Asp Ser Val Pro Pro Phe Thr Pro Asp Phe Glu Gly Ala
305                 310                 315                 320

ACC GAC ACA TGC AAC TTC GAC TTG GTG GAG GAC GGG CTC ACT GCC ATG     1008
Thr Asp Thr Cys Asn Phe Asp Leu Val Glu Asp Gly Leu Thr Ala Met
                325                 330                 335

GAG ACA CTG TCG GAC ATT CGG GAA GGT GCG CCG CTA GGG GTC CAC CTG     1056
Glu Thr Leu Ser Asp Ile Arg Glu Gly Ala Pro Leu Gly Val His Leu
            340                 345                 350

CCT TTT GTG GGC TAC TCC TAC TCC TGC ATG GCC CTC AGG GAC AGT GAG     1104
Pro Phe Val Gly Tyr Ser Tyr Ser Cys Met Ala Leu Arg Asp Ser Glu
        355                 360                 365

GTC CCA GGC CCC ACA CCC ATG GAA GTG GAG GCC GAG CAG CTG CTT GAG     1152
Val Pro Gly Pro Thr Pro Met Glu Val Glu Ala Glu Gln Leu Leu Glu
    370                 375                 380

CCA CAC GTG CAA GCG CCC AGC CTG GAG CCC TCG GTG TCC CCA CAG GAT     1200
Pro His Val Gln Ala Pro Ser Leu Glu Pro Ser Val Ser Pro Gln Asp
385                 390                 395                 400

GAA ACA GCT GAA GTG GCA GTT CCA GCG GCT GTC CCT GCG GCA GAG GCT     1248
Glu Thr Ala Glu Val Ala Val Pro Ala Ala Val Pro Ala Ala Glu Ala
                405                 410                 415

GAG GCC GAG GTG ACG CTG CGG GAG CTC CAG GAA GCC CTG GAG GAG GAG     1296
Glu Ala Glu Val Thr Leu Arg Glu Leu Gln Glu Ala Leu Glu Glu Glu
            420                 425                 430

GTG CTC ACC CGG CAG AGC CTG AGC CGG GAG ATG GAG GCC ATC CGC ACG     1344
Val Leu Thr Arg Gln Ser Leu Ser Arg Glu Met Glu Ala Ile Arg Thr
        435                 440                 445

GAC AAC CAG AAC TTC GCC AGT CAA CTA CGC GAG GCA GAG GCT CGG AAC     1392
Asp Asn Gln Asn Phe Ala Ser Gln Leu Arg Glu Ala Glu Ala Arg Asn
    450                 455                 460

CGG GAC CTA GAG GCA CAC GTC CGG CAG TTG CAG GAG CGG ATG GAG TTG     1440
Arg Asp Leu Glu Ala His Val Arg Gln Leu Gln Glu Arg Met Glu Leu
465                 470                 475                 480

CTG CAG GCA GAG GGA GCC ACA GCT GTC ACG GGG GTC CCC AGT CCC CGG     1488
Leu Gln Ala Glu Gly Ala Thr Ala Val Thr Gly Val Pro Ser Pro Arg
                485                 490                 495

GCC ACG GAT CCA CCT TCC CAT CTA GAT GGC CCC CCG GCG TGG CTG TGG     1536
Ala Thr Asp Pro Pro Ser His Leu Asp Gly Pro Pro Ala Trp Leu Trp
            500                 505                 510

GCC AGT GCC CGC TGG TGG GGC CAG GCC ATG CAC CGC CGC CAC CTG CTG     1584
Ala Ser Ala Arg Trp Trp Gly Gln Ala Met His Arg Arg His Leu Leu
        515                 520                 525

CTC CCT GCC AGG GTC CCT AGG CCT GGC CTA TCG GAG GCG CTT TCC CTG     1632
Leu Pro Ala Arg Val Pro Arg Pro Gly Leu Ser Glu Ala Leu Ser Leu
    530                 535                 540

CTC CTG TTC GCC GTT GTT CTG TCT CGT GCC GCC GCC CTG GGC TGC ATT     1680
Leu Leu Phe Ala Val Val Leu Ser Arg Ala Ala Ala Leu Gly Cys Ile
545                 550                 555                 560

GGG TTG GTG GCC CAC GCC GGC CAA CTC ACC GCA GTC TGG CGC CGC CCA     1728
Gly Leu Val Ala His Ala Gly Gln Leu Thr Ala Val Trp Arg Arg Pro
                565                 570                 575

GGA GCC GCC CGC GCT CCC TGAACCCTAG AACTGTCTTC GACTCCGGGG            1776
Gly Ala Ala Arg Ala Pro
                580

CCCCGTTGGA AGACTGAGTG CCCGGGGCCA GCACAGAAGC CGCGCCCACC GCCTGCCAGT   1836

TCACAACCGC TCCGAGCGTG GGTCTCCGCC CAGCTCCAGT CCTGTGATCC GGGCCCGCCC   1896
```

```
CCTAGCGGCC GGGGAGGGAG GGGCCGGGTC CGCGGCCGGC GAACGGGGCT CGAAGGGTCC    1956

TTGTAGCCGG GAATGCTGCT GCTGCTGCTG CTGCTGCTGC TGCTGCTGGG GGGATCACAG    2016

ACCATTTCTT TCTTTCGGCC AGGCTGAGGC CCTGACGTGG ATGGGCAAAC TGCAGGCCTG    2076

GGAAGGCAGC AAGCCGGGCC GTCCGTGTTC CATCCTCCAC GCACCCCCAC CTATCGTTGG    2136

TTCGCAAAGT GCAAAGCTTT CTTGTGCATG ACGCCCTGCT CTGGGGAGCG TCTGGCGCGA    2196

TCTCTGCCTG CTTACTCGGG AAATTTGCTT TTGCCAAACC CGCTTTTTCG GGGATCCCGC    2256

GCCCCCCTCC TCACTTGCGC TGCTCTCGGA GCCCCAGCCG GCTCCGCCGC CTTCGGCGGT    2316

TTGGATATTT ATTGACCTCG TCCTCCGACT CGCTGACAGG CTACAGGACC CCCAACAACC    2376

CCAATCCACG TTTTGGATGC ACTGAGACCC CGACATTCCT CGGTATTTAT TGTCTGTCCC    2436

CACCTAGGAC CCCCACCCCC GACCCTCGCG AATAAAAGGC CCTCCATCTG CCCAAAAAAA    2496

AAAAAAAAAA AAAAA                                                    2511
```

(2) INFORMATION FOR SEQ ID NO:9:

(i) SEQUENCE CHARACTERISTICS:
        (A) LENGTH: 582 amino acids
        (B) TYPE: amino acid
        (D) TOPOLOGY: linear (ii) MOLECULE TYPE: protein (xi) SEQUENCE DESCRIPTION: SEQ ID NO:9:

```
Pro Pro Gly Gln Val Arg Gly Arg Leu Leu Ala Val Gly Gly Ala Ile
  1               5                  10                  15

Val Val Arg Leu Lys Glu Val Arg Leu Gln Arg Asp Asp Phe Glu Ile
                 20                  25                  30

Leu Lys Val Ile Gly Arg Gly Ala Phe Ser Glu Val Ala Val Val Lys
         35                  40                  45

Met Lys Gln Thr Gly Gln Val Tyr Ala Met Lys Ile Met Asn Lys Trp
     50                  55                  60

Asp Met Leu Lys Arg Gly Glu Val Ser Cys Phe Arg Glu Glu Arg Asp
 65                  70                  75                  80

Val Leu Val Asn Gly Asp Arg Arg Trp Ile Thr Gln Leu His Phe Ala
                 85                  90                  95

Phe Gln Asp Glu Asn Tyr Leu Tyr Leu Val Met Glu Tyr Tyr Val Gly
            100                 105                 110

Gly Asp Leu Leu Thr Leu Leu Ser Lys Phe Gly Glu Arg Ile Pro Ala
        115                 120                 125

Glu Met Ala Arg Phe Tyr Leu Ala Glu Ile Val Met Ala Ile Asp Ser
    130                 135                 140

Val His Arg Leu Gly Tyr Val His Arg Asp Ile Lys Pro Asp Asn Ile
145                 150                 155                 160

Leu Leu Asp Arg Cys Gly His Ile Arg Leu Ala Asp Phe Gly Ser Cys
                165                 170                 175

Leu Lys Leu Arg Ala Asp Gly Thr Val Arg Ser Leu Val Ala Val Gly
            180                 185                 190

Thr Pro Asp Tyr Leu Ser Pro Glu Ile Leu Gln Ala Val Gly Gly Gly
        195                 200                 205

Pro Gly Thr Gly Ser Tyr Gly Pro Glu Cys Asp Trp Trp Ala Leu Gly
    210                 215                 220

Val Phe Ala Tyr Glu Met Phe Tyr Gly Gln Thr Pro Phe Tyr Ala Asp
225                 230                 235                 240
```

-continued

```
Ser Thr Ala Glu Thr Tyr Gly Lys Ile Val His Tyr Lys Glu His Leu
             245                 250                 255

Ser Leu Pro Leu Val Asp Glu Gly Val Pro Glu Glu Ala Arg Asp Phe
             260                 265                 270

Ile Gln Arg Leu Leu Cys Pro Pro Glu Thr Arg Leu Gly Arg Gly Gly
             275                 280                 285

Ala Gly Asp Phe Arg Thr His Pro Phe Phe Gly Leu Asp Trp Asp
             290                 295                 300

Gly Leu Arg Asp Ser Val Pro Pro Phe Thr Pro Asp Phe Glu Gly Ala
305                 310                 315                 320

Thr Asp Thr Cys Asn Phe Asp Leu Val Glu Asp Gly Leu Thr Ala Met
                 325                 330                 335

Glu Thr Leu Ser Asp Ile Arg Glu Gly Ala Pro Leu Gly Val His Leu
                 340                 345                 350

Pro Phe Val Gly Tyr Ser Tyr Ser Cys Met Ala Leu Arg Asp Ser Glu
             355                 360                 365

Val Pro Gly Pro Thr Pro Met Glu Val Glu Ala Glu Gln Leu Leu Glu
             370                 375                 380

Pro His Val Gln Ala Pro Ser Leu Glu Pro Ser Val Ser Pro Gln Asp
385                 390                 395                 400

Glu Thr Ala Glu Val Ala Val Pro Ala Ala Val Pro Ala Ala Glu Ala
                 405                 410                 415

Glu Ala Glu Val Thr Leu Arg Glu Leu Gln Glu Ala Leu Glu Glu Glu
                 420                 425                 430

Val Leu Thr Arg Gln Ser Leu Ser Arg Glu Met Glu Ala Ile Arg Thr
             435                 440                 445

Asp Asn Gln Asn Phe Ala Ser Gln Leu Arg Glu Ala Glu Ala Arg Asn
             450                 455                 460

Arg Asp Leu Glu Ala His Val Arg Gln Leu Gln Glu Arg Met Glu Leu
465                 470                 475                 480

Leu Gln Ala Glu Gly Ala Thr Ala Val Thr Gly Val Pro Ser Pro Arg
                 485                 490                 495

Ala Thr Asp Pro Pro Ser His Leu Asp Gly Pro Pro Ala Trp Leu Trp
             500                 505                 510

Ala Ser Ala Arg Trp Trp Gly Gln Ala Met His Arg Arg His Leu Leu
             515                 520                 525

Leu Pro Ala Arg Val Pro Arg Pro Gly Leu Ser Glu Ala Leu Ser Leu
             530                 535                 540

Leu Leu Phe Ala Val Val Leu Ser Arg Ala Ala Ala Leu Gly Cys Ile
545                 550                 555                 560

Gly Leu Val Ala His Ala Gly Gln Leu Thr Ala Val Trp Arg Arg Pro
                 565                 570                 575

Gly Ala Ala Arg Ala Pro
             580
```

(2) INFORMATION FOR SEQ ID NO:10:

(i) SEQUENCE CHARACTERISTICS:
        (A) LENGTH: 3323 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_difference
        (B) LOCATION: replace(518..3323, "")

(D) OTHER INFORMATION: /standard_name= "cDNA 41"

(ix) FEATURE:
         (A) NAME/KEY: misc_difference
         (B) LOCATION: replace(769..3323, "")
         (D) OTHER INFORMATION: /standard_name= "cDNA 28"

(xi) SEQUENCE DESCRIPTION: SEQ ID NO:10:

| | | | | | |
|---|---|---|---|---|---|
| AAAAAAAAAA | AAGCTGGTAT | AAAGCAGAGA | GCCTGAGGGC | TAAATTTAAC | TGTCCGAGTC | 60 |
| GGAATCCATC | TCTGAGTCAC | CCAAGAAGCT | GCCCTGGCCT | CCCGTCCCCT | TCCCAGGCCT | 120 |
| CAACCCCTTT | CTCCCACCCA | GCCCCAACCC | CCAGCCCTCA | CCCCCTAGCC | CCCAGTTCTG | 180 |
| GAGCTTGTCG | GGAGCAAGGG | GGTGGTTGCT | ACTGGGTCAC | TCAGCCTCAA | TTGGCCCTGT | 240 |
| TTCAGCAATG | GGCAGGTTCT | TCTTGAAATT | CATCACACCT | GTGGCTTCCT | CTGTGCTCTA | 300 |
| CCTTTTTATT | GGGGTGACAG | TGTGACAGCT | GAGATTCTCC | ATGCATTCCC | CCTACTCTAG | 360 |
| CACTGAAGGG | TTCTGAAGGG | CCCTGGAAGG | AGGGAGCTTG | GGGGGCTGGC | TTGTGAGGGG | 420 |
| TTAAGGCTGG | GAGGCGGGAG | GGGGGCTGGA | CCAAGGGGTG | GGGAGAAGGG | GAGGAGGCCT | 480 |
| CGGCCGGCCG | CAGAGAGAAG | TGGCCAGAGA | GGCCCAGGGG | GACAGCCAGG | GACAGGCAGA | 540 |
| CATGCAGCCA | GGGCTCCAGG | GCCTGGACAG | GGGCTGCCAG | GCCCTGTGAC | AGGAGGACCC | 600 |
| CGAGCCCCCG | GCCCGGGGAG | GGGCCATGGT | GCTGCCTGTC | AACATGTCA | GCCGAGGTGC | 660 |
| GGCTGAGGCG | GCTCCAGCAG | CTGGTGTTGG | ACCCGGGCTT | CCTGGGGCTG | GAGCCCCTGC | 720 |
| TCGACCTTCT | CCTGGGCGTC | CACCAGGAGC | TGGGCGCCTC | CGAACTGGCC | CAGGACAAGT | 780 |
| ACGTGGCCGA | CTTCTTGCAG | NNNTGGGCGG | AGCCCATCGT | GGTGAGGCTT | AAGGAGGTCC | 840 |
| GACTGCAGAG | GGACGACTTC | GAGATTCTGA | AGGTGATCGG | ACGCGGGGCG | TTCAGCGNNN | 900 |
| AGGTAGCGGT | AGTGAAGATG | AAGCAGACGG | GCCAGGTGTA | TGCCATGAAG | ATCATGAACA | 960 |
| AGTGGGACAT | GCTGAAGAGG | GGCGAGNNNG | TGTCGTGCTT | CCGTGAGGAG | AGGGACGTGT | 1020 |
| TGGTGAATGG | GGACCGGCGG | TGGATCACGC | AGCTGCACTT | CGCCTTCCAG | GATGAGAACT | 1080 |
| ACCTGNNNTA | CCTGGTCATG | GAGTATTACG | TGGGCGGGGA | CCTGCTGACA | CTGCTGAGCA | 1140 |
| AGTTTGGGGA | GCGGATTCCG | GCCGAGATGG | CGCGCTTCTA | CCTGGCGGAG | ATTGTCATGG | 1200 |
| CCATAGACTC | GGTGCACCGG | CTTGGCTACG | TGCACAGNNN | GGACATCAAA | CCCGACAACA | 1260 |
| TCCTGCTGGA | CCGCTGTGGC | CACATCCGCC | TGGCCGACTT | CGGTCTTGC | CTCAAGCTGC | 1320 |
| GGGCAGATGG | AACGNNNGTG | CGGTCGCTGG | TGGCTGTGGG | CACCCCAGAC | TACCTGTCCC | 1380 |
| CCGAGATCCT | GCAGGCTGTG | GGCGGTGGGC | CTGGGACAGG | CAGCTACGGG | CCCGAGTGTG | 1440 |
| ACTGGTGGGC | GCTGGGTGTA | TTCGCCTATG | AAATGTTCTA | TGGGCAGACG | CCCTTCTACG | 1500 |
| CGGATTCCAC | GGCGGAGACC | TATGGCAAGA | TCGTCCACTA | NNNCAAGGAG | CACCTCTCTC | 1560 |
| TGCCGCTGGT | GGACGAAGGG | GTCCCTGAGG | AGGCTCGAGA | CTTCATTCAG | CGGTTGCTGT | 1620 |
| GTCCCCCGGA | GACACGGCTG | GGCCGGGGTG | GAGCAGGCGA | CTTCCGGACA | CATCCCTTCT | 1680 |
| TCTTTGGCCT | CGACTGGGAT | GGTCTCCGGG | ACAGCGTGCC | CCCCTTTACA | CCGGATTTCG | 1740 |
| AAGGTGCCAC | CGACACATGC | AACTTCGACT | TGGTGGAGAA | CGGGCTCACT | GCCATGNNNG | 1800 |
| AGACACTGTC | GGACATTCGG | GAAGGTGCGC | CGCTAGGGGT | CCACCTGCCT | TTTGTGGGCT | 1860 |
| ACTCCTACTC | CTGCATGGCC | CTCAGNNNGG | ACAGTGAGGT | CCCAGGCCCC | ACACCCATGG | 1920 |
| AAGTGGAGGC | CGAGCAGCTG | CTTGAGCCAC | ACGTGCAAGC | GCCCAGCCTG | GAGCCCTCGG | 1980 |
| TGTCCCCACA | GGATGAAACA | NNNGCTGAAG | TGGCAGTTCC | AGCGGCTGTC | CCTGCGGCAG | 2040 |
| AGGCTGAGGC | CGAGGTGACG | CTGCGGGAGC | TCCAGGAAGC | CCTGGAGGAG | GAGGTGCTCA | 2100 |
| CCCGGCAGAG | CCTGAGCCGG | GAGATGGAGG | CCATCCGCAC | GGACAACCAG | AACTTCGCCA | 2160 |

```
GNNNTCAACT ACGCGAGGCA GAGGCTCGGA ACCGGGACCT AGAGGCACAC GTCCGGCAGT    2220

TGCAGGAGCG GATGGAGTTG CTGCAGGCAG AGGGAGCCAC AGNNNCTGTC ACGGGGGTCC    2280

CCAGTCCCCG GGCCACGGAT CCACCTTCCC ATNNNCTAGA TGGCCCCCCG GCCGTGGCTG    2340

TGGGCCAGTG CCCGCTGGTG GGGCCAGGCC CCATGCACCG CCGCCACCTG CTGCTCCCTG    2400

CCAGGNNNGT CCCTAGGCCT GGCCTATCGG AGGCGCTTTC CCTGCTCCTG TTCGCCGTTG    2460

TTCTGTCTCG TGCCGCCGCC CTGGGCTGCA TTGGGTTGGT GGCCCACGCC GGCCAACTCA    2520

CCGCAGTCTG GCGCCGCCCA GGAGCCGCCC GCGCTCCCTG AACCCTAGAA CTGTCTTCGA    2580

CTCCGGGGCC CCGTTGGAAG ACTGAGTGCC CGGGGCCAGC ACAGAAGCCG CGCCCACCGC    2640

CTGCCAGTTC ACAACCGCTC CGAGCGTGGG TCTCCGCCCA GCTCCAGTCC TGTGATCCGG    2700

GCCCGCCCCC TAGCGGCCGG GGAGGGAGGG GCCGGGTCCG CGGCCGGCGA ACGGGCTCG    2760

AAGGGTCCTT GTAGCCGGGA ATGCTGCTGC TGCTGCTGCT GCTGCTGCTG CTGCTGGGGG    2820

CATCACAGAC CATTTCTTTC TTTCGGCCAG GCTGAGGCCC TGACGTGGAT GGGCAAACTG    2880

CAGGCCTGGG AAGGCAGCAA GCCGGGCCGT CCGTGTTCCA TCCTCCACGC ACCCCCACCT    2940

ATCGTTGGTT CGCAAAGTGC AAAGCTTTCT TGTGCATGAC GCCCTGCTCT GGGGAGCGTC    3000

TGGCGCGATC TCTGCCTGGT TACTCGGGAA ATTTGCTTTT GCCAAACCCG CTTTTTCGGG    3060

GATCCCGCGC CCCCCTCCTC ACTTGCGCTG CTCTCGGAGC CCCAGCCGGC TCCGCCGCCT    3120

TCGGCGGTTT GGATATTTAT TGACCTCGTC CTCCGACTCG CTGACAGGCT ACAGGACCCC    3180

CAACAACCCC AATCCACGTT TTGGATGCAC TGAGACCCCG ACATTCCTCG GTATTTATTG    3240

TCTGTCCCCA CCTAGGACCC CCACCCCCGA CCCTCGCGAA TAAAAGGCCC TCCATCTGCC    3300

CAAAAAAAAA AAAAAAAAA AAA                                             3323

(2) INFORMATION FOR SEQ ID NO:11:

(i) SEQUENCE CHARACTERISTICS:
        (A) LENGTH: 638 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

Met Ser Ala Glu Val Arg Leu Arg Arg Leu Gln Gln Leu Val Leu Asp
1               5                   10                  15

Pro Gly Phe Leu Gly Leu Glu Pro Leu Leu Asp Leu Leu Gly Val
            20                  25                  30

His Gln Glu Leu Gly Ala Ser Glu Leu Ala Gln Asp Lys Tyr Val Ala
            35                  40                  45

Asp Phe Leu Gln Xaa Trp Ala Glu Pro Ile Val Arg Leu Lys Glu
50                  55                  60

Val Arg Leu Gln Arg Asp Asp Phe Glu Ile Leu Lys Val Ile Gly Arg
65                  70                  75                  80

Gly Ala Phe Ser Xaa Xaa Val Ala Val Val Lys Met Lys Gln Thr Gly
                85                  90                  95

Gln Val Tyr Ala Met Lys Ile Met Asn Lys Trp Asp Met Leu Lys Arg
            100                 105                 110

Gly Glu Xaa Val Ser Cys Phe Arg Glu Glu Arg Asp Val Leu Val Asn
            115                 120                 125

Gly Asp Arg Arg Trp Ile Thr Gln Leu His Phe Ala Phe Gln Asp Glu
130                 135                 140
```

-continued

```
Asn Tyr Leu Xaa Tyr Leu Val Met Glu Tyr Tyr Val Gly Gly Asp Leu
145                 150                 155                 160

Leu Thr Leu Leu Ser Lys Phe Gly Glu Arg Ile Pro Ala Glu Met Ala
            165                 170                 175

Arg Phe Tyr Leu Ala Glu Ile Val Met Ala Ile Asp Ser Val His Arg
            180                 185                 190

Leu Gly Tyr Val His Xaa Xaa Asp Ile Lys Pro Asp Asn Leu Leu Leu
            195                 200                 205

Asp Arg Cys Gly His Ile Arg Leu Ala Asp Phe Gly Ser Cys Leu Lys
            210                 215                 220

Leu Arg Ala Asp Gly Thr Xaa Val Arg Ser Leu Val Ala Val Gly Thr
225                 230                 235                 240

Pro Asp Tyr Leu Ser Pro Glu Ile Leu Gln Ala Val Gly Gly Gly Pro
            245                 250                 255

Gly Thr Gly Ser Tyr Gly Pro Glu Cys Asp Trp Trp Ala Leu Gly Val
            260                 265                 270

Phe Ala Tyr Glu Met Phe Tyr Gly Gln Thr Pro Phe Tyr Ala Asp Ser
            275                 280                 285

Thr Ala Glu Thr Tyr Gly Lys Ile Val His Xaa Xaa Lys Glu His Leu
290                 295                 300

Ser Leu Pro Leu Val Asp Glu Gly Val Pro Glu Glu Ala Arg Asp Phe
305                 310                 315                 320

Ile Gln Arg Leu Leu Cys Pro Pro Glu Thr Arg Leu Gly Arg Gly Gly
            325                 330                 335

Ala Gly Asp Phe Arg Thr His Pro Phe Phe Gly Leu Asp Trp Asp
            340                 345                 350

Gly Leu Arg Asp Ser Val Pro Pro Phe Thr Pro Asp Phe Glu Gly Ala
            355                 360                 365

Thr Asp Thr Cys Asn Phe Asp Leu Val Glu Asp Gly Leu Thr Ala Met
            370                 375                 380

Xaa Glu Thr Leu Ser Asp Ile Arg Glu Gly Ala Pro Leu Gly Val His
385                 390                 395                 400

Leu Pro Phe Val Gly Tyr Ser Tyr Ser Cys Met Ala Leu Xaa Xaa Asp
            405                 410                 415

Ser Glu Val Pro Gly Pro Thr Pro Met Glu Val Glu Ala Glu Gln Leu
            420                 425                 430

Leu Glu Pro His Val Gln Ala Pro Ser Leu Glu Pro Ser Val Ser Pro
            435                 440                 445

Gln Asp Glu Thr Xaa Ala Glu Val Ala Val Pro Ala Ala Val Pro Ala
450                 455                 460

Ala Glu Ala Glu Ala Glu Val Thr Leu Arg Glu Leu Gln Glu Ala Leu
465                 470                 475                 480

Glu Glu Glu Val Leu Thr Arg Gln Ser Leu Ser Arg Glu Met Glu Ala
            485                 490                 495

Ile Arg Thr Asp Asn Gln Asn Phe Ala Xaa Xaa Gln Leu Arg Glu Ala
            500                 505                 510

Glu Ala Arg Asn Arg Asp Leu Glu Ala His Val Arg Gln Leu Gln Glu
            515                 520                 525

Arg Met Glu Leu Leu Gln Ala Glu Gly Ala Thr Xaa Xaa Val Thr Gly
            530                 535                 540

Val Pro Ser Pro Arg Ala Thr Asp Pro Pro Ser His Xaa Leu Asp Gly
545                 550                 555                 560

Pro Pro Ala Val Ala Val Gly Gln Cys Pro Leu Val Gly Pro Gly Pro
```

```
                565                  570                  575
Met His Arg Arg His Leu Leu Leu Pro Ala Arg Xaa Val Pro Arg Pro
                580                  585                  590

Gly Leu Ser Glu Ala Leu Ser Leu Leu Leu Phe Ala Val Val Leu Ser
                595                  600                  605

Arg Ala Ala Ala Leu Gly Cys Ile Gly Leu Val Ala His Ala Gly Gln
            610                  615                  620

Leu Thr Ala Val Trp Arg Arg Pro Gly Ala Ala Arg Ala Pro
625                  630                  635
```

(2) INFORMATION FOR SEQ ID NO:12:

(i) SEQUENCE CHARACTERISTICS:
        (A) LENGTH: 2726 base pairs
        (B) TYPE: nucleic acid
        (C) STRANDEDNESS: double
        (D) TOPOLOGY: linear (xi) SEQUENCE DESCRIPTION: SEQ ID NO:12:

```
GGGGACAGCC AGGGACAGGC AGACATGCAG CCAGGGCTCC AGGGCCTGGA CAGGGGCTGC    60
CAGGCCCTGT GACAGGAGGA CCCCGAGCCC CCGGCCCGGG GAGGGGCCAT GGTGCTGCCT   120
GTCCAACATG TCAGCCGAGG TGCGGCTGAG GCGGCTCCAG CAGCTGGTGT TGGACCCGGG   180
CTTCCTGGGG CTGGAGCCCC TGCTCGACCT TCTCCTGGGC GTCCACCAGG AGCTGGGCGC   240
CTCCGAACTG GCCCAGGACA AGTACGTGGC CGACTTCTTG CAGTGGGCGG AGCCCATCGT   300
GGTGAGGCTT AAGGAGGTCC GACTGCAGAG GGACGACTTC GAGATTCTGA AGGTGATCGG   360
ACGCGGGGCG TTCAGCGAGG TAGCGGTAGT GAAGATGAAG CAGACGGGCC AGGTGTATGC   420
CATGAAGATC ATGAACAAGT GGGACATGCT GAAGAGGGGC GAGGTGTCGT GCTTCCGTGA   480
GGAGAGGGAC GTGTTGGTGA ATGGGGACCG GCGGTGGATC ACGCAGCTGC ACTTCGCCTT   540
CCAGGATGAG AACTACCTGT ACCTGGTCAT GGAGTATTAC GTGGGCGGGG ACCTGCTGAC   600
ACTGCTGAGC AAGTTTGGGG AGCGGATTCC GGCCGAGATG GCGCGCTTCT ACCTGGCGGA   660
GATTGTCATG GCCATAGACT CGGTGCACCG GCTTGGCTAC GTGCACAGGG ACATCAAACC   720
CGACAACATC CTGCTGGACC GCTGTGGCCA CATCCGCCTG GCCGACTTCG GCTCTTGCCT   780
CAAGCTGCGG GCAGATGGAA CGGTGCGGTC GCTGGTGGCT GTGGGCACCC CAGACTACCT   840
GTCCCCCGAG ATCCTGCAGG CTGTGGGCGG TGGGCCTGGG ACAGGCAGCT ACGGGCCCGA   900
GTGTGACTGG TGGGCGCTGG GTGTATTCGC CTATGAAATG TTCTATGGGC AGACGCCCTT   960
CTACGCGGAT TCCACGGCGG AGACCTATGG CAAGATCGTC CACTACAAGG AGCACCTCTC  1020
TCTGCCGCTG GTGACGAAGG GGGTCCCTGA GGAGGCTCGA GACTTCATTC AGCGGTTGCT  1080
GTGTCCCCCG GAGACACGGC TGGGCCGGGG TGGAGCAGGC GACTTCCGGA CACATCCCTT  1140
CTTCTTTGGC CTCGACTGGG ATGGTCTCCG GGACAGCGTG CCCCCCTTTA CACCGGATTT  1200
CGAAGGTGCC ACCGACACAT GCAACTTCGA CTTGGTGGAG GACGGGCTCA CTGCCATGGA  1260
GACACTGTCG GACATTCGGG AAGGTGCGCC GCTAGGGGTC CACCTGCCTT TTGTGGGCTA  1320
CTCCTACTCC TGCATGGCCC TCAGGGACAG TGAGGTCCCA GGCCCACACA CCATGGAAGT  1380
GGAGGCCGAG CAGCTGCTTG AGCCACACGT GCAAGCGCCC AGCCTGGAGC CTCGGTGTC   1440
CCCACAGGAT GAAACAGCTG AAGTGGCAGT TCCAGCGGCT GTCCCTGCGG CAGAGGCTGA  1500
GGCCGAGGTG ACGCTGCGGG AGCTCCAGGA AGCCCTGGAG GAGGAGGTGC TCACCCGGCA  1560
GAGCCTGAGC CGGGAGATGG AGGCCATCCG CACGGACAAC CAGAACTTCG CCAGTCAACT  1620
ACGCGAGGCA GAGGCTCGGA ACCGGGACCT AGAGGCACAC GTCCGGCAGT TGCAGGAGCG  1680
```

```
GATGGAGTTG CTGCAGGCAG AGGGAGCCAC AGCTGTCACG GGGGTCCCCA GTCCCCGGGC    1740

CACGGATCCA CCTTCCCATC TAGATGGCCC CCCGGCCGTG GCTGTGGGCC AGTGCCCGCT    1800

GGTGGGGCCA GGCCCCATGC ACCGCCGCCA CCTGCTGCTC CCTGCCAGGG TCCCTAGGCC    1860

TGGCCTATCG GAGGCGCTTT CCCTGCTCCT GTTCGCCGTT GTTCTGTCTC GTGCCGCCGC    1920

CCTGGGCTGC ATTGGGTTGG TGGCCCACGC CGGCCAACTC ACCGCAGTCT GGCGCCGCCC    1980

AGGAGCCGCC CGCGCTCCCT GAACCCTAGA ACTGTCTTCG ACTCCGGGGC CCCGTTGGAA    2040

GACTGAGTGC CCGGGGCCAG CACAGAAGCC GCGCCCACCG CCTGCCAGTT CACAACCGCT    2100

CCGAGCGTGG GTCTCCGCCC AGCTCCAGTC CTGTGATCCG GGCCCGCCCC CTAGCGGCCG    2160

GGGAGGGAGG GGCCGGGTCC GCGGCCGGCG AACGGGCTC GAAGGGTCCT TGTAGCCGGG     2220

AATGCTGCTG CTGCTGCTGC TGCTGCTGCT GCTGCTGGGG GGATCACAGA CCATTTCTTT    2280

CTTTCGGCCA GGCTGAGGCC CTGACGTGGA TGGGCAAACT GCAGGCCTGG GAAGGCAGCA    2340

AGCCGGGCCG TCCGTGTTCC ATCCTCCACG CACCCCCACC TATCGTTGGT TCGCAAAGTG    2400

CAAAGCTTTC TTGTGCATGA CGCCCTGCTC TGGGGAGCGT CTGGCGCGAT CTCTGCCTGC    2460

TTACTCGGGA AATTTGCTTT TGCCAAACCC GCTTTTTCGG GGATCCCGCG CCCCCCTCCT    2520

CACTTGCGCT GCTCTCGGAG CCCCAGCCGG CTCCGCCGCC TTCGGCGGTT TGGATATTTA    2580

TTGACCTCGT CCTCCGACTC GCTGACAGGC TACAGGACCC CCAACAACCC CAATCCACGT    2640

TTTGGATGCA CTGAGACCCC GACATTCCTC GGTATTTATT GTCTGTCCCC ACCTAGGACC    2700

CCCACCCCCG ACCCTCGCGA ATAAAA                                        2726

(2) INFORMATION FOR SEQ ID NO:13:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GGATTACAGG YRTGAGCCA                                                  19

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

RCCAYTGCAC TCCAGCCTG                                                  19
```

DNA SEQUENCE ENCODING THE MYOTONIC DYSTROPHY GENE AND USES THEREOF

RELATED APPLICATION

This application is a continuation-in-part of U.S. Ser. No. 08/284,543, (entitled "Nucleotide Sequences and Materials and Methods for the Diagnosis of Myotonic Dystrophy" by Duncan James Shaw, Helen Grace Harley, Keith Jack Johnson, John David Brook, and David E. Housman), filed Aug. 8, 1994, now abandoned, which is the U.S. national phase of PCT/GB93/00253, (entitled "Nucleotide Sequences and Materials and Methods for the Diagnosis of Myotonic Dystrophy" by Duncan James Shaw, Helen Grace Harley, Keith Jack Johnson, John David Brook, and David E. Housman), filed Feb. 5, 1993, which claims priority to GB9202485.0, (entitled "DNA Sequences and Materials and Methods for the Diagnosis of Myotonic Dystrophy", filed Feb. 6, 1992. This application also claims priority as a continuation-in-part application to U.S. Ser. No. 08/023,612, (entitled "DNA Sequence Encoding the Myotonic Dystrophy Gene and Uses Thereof" by J. David Brook and David E. Housman), filed Feb. 26, 1993, now abandoned, which is a continuation-in-part of Ser. No. 07/839,255, filed Feb. 20, 1992, (entitled "Myotonic Dystrophy: Expansion of a Trinucleotide (CTG) Repeat at the 3' End of a Transcript Encoding a Protein Kinase Family Member" by J. David Brook and David E. Housman), now abandoned, and also claims priority under 35 U.S.C. 119 to PCT/US93/01545, filed Feb. 19, 1993, (entitled "DNA Sequence Encoding the Myotonic Dystrophy Gene and Uses Thereof" by J. David Brook and David E. Housman). The teachings of all the cited applications are expressly incorporated herein by reference in their entirety.

GOVERNMENT SUPPORT

This invention was made in whole or in part with U.S. Government support under Grant Number NIH-P01-HL-41484 awarded by the National Institutes of Health. The United States Government has certain rights in the invention.

BACKGROUND

Myotonic dystrophy (DM) is an autosomal dominant neuromuscular disease with an estimated minimum incidence of 1 in 8000 (Harper, P. S., *Myotonic Dystrophy*, 2nd ed., W. B. Saunders Co., London, 1989). It is the most common form of muscular dystrophy affecting adults. The clinical picture in DM is well established but exceptionally variable (Harper, P. S., *Myotonic Dystrophy*, 2nd ed., W. B. Saunders Co., London, 1989). Although generally considered a disease of muscle, with myotonia, progressive weakness and wasting, DM is characterized by abnormalities in a variety of other systems. DM patients often suffer from cardiac conduction defects, smooth muscle involvement, hypersomnia, cataracts, abnormal glucose response, and, in males, premature balding and testicular atrophy (Harper, P. S., *Myotonic Dystrophy*, 2nd ed., W. B. Saunders Co., London, 1989). One of the striking features of this disorder is the variability of phenotype, both within and between families. For clinical purposes, patients are often subdivided into three groups according to the clinical syndrome and age at onset of the disorder (Harper, P. S. and Dyken, P. R., *Lancet*, 2:53–55 (1972)). The mildest form, which is occasionally difficult to diagnose, is seen in middle or old age and is characterized by cataracts with little or no muscle involvement. The classical form, showing myotonia and muscle weakness, most frequently has onset in early adult life and in adolescence. The most severe form, which occurs congenitally, is associated with generalized muscular hypoplasia, mental retardation, and high neonatal mortality. Those congenitally affected offspring surviving the neonatal period invariably exhibit the classical form of the disease in late childhood or adolescence. The congenital form of DM is almost exclusively maternally transmitted. The phenomenon of anticipation (Howeler, C. J. et al., *Brain*, 112:779–797 (1989)), in which the disease symptoms become more severe and age at onset earlier in successive generations, is often most strikingly manifested in a family producing a congenitally affected child.

To date this disease has been untreatable and its biochemical basis is not understood. Biochemical studies have failed to identify the defective protein in myotonic dystrophy, although several have implicated defects in membrane structure and function (Harper, P. S., *Myotonic Dystrophy*, 2nd ed., W. B. Saunders Co., London, 1989). Abnormalities in calcium transport (Seiler, D. and Kuhn, E., *Schweitz Med. Wochenschr.* 100:1374–1376 (1970)), membrane fluidity (Butterfield, D. A. et al., *Biochemistry*, 13:5078–5082 (1974)), sodium-potassium ATPase stoichiometry (Hull, K. L., Jr. and Roses, A. D., *J. Physiol.*, 254:169–181 (1976)), and apamin receptor expression (Renaud, J. F. et al., *Nature* 319:676–680 (1986)) have all been reported for DM. There is also evidence of reduced phosphorylation of membrane proteins in both red blood cells (Roses, A. D. and Appel, S. H., *Proc. Natl. Acad. Sci.* USA 70:1855–1859 (1973)) and sarcolemmal membranes from muscle biopsies of patients (Roses, A. D. and Appel, S. H., *Nature* 250:245–247 (1974)).

A better understanding of the underlying mechanism of DM would be very valuable in diagnosing and, ultimately, treating or preventing DM.

SUMMARY OF THE INVENTION

Applicants have identified a CTG triplet repeat, present on chromosome 19, which undergoes expansion in myotonic dystrophy (DM) patients. They have also shown that the normal population exhibits great variability (instability) in this sequence, which is present in unaffected individuals in 5–40 copies; that DM patients who are minimally affected have at least 50 CTG repeats; and that more severely affected patients have expansion of the repeat-containing segment up to several kilobase (kb) pairs.

In addition, Applicants have demonstrated that the CTG repeat is transcribed and is located in the 3' untranslated region of an mRNA which encodes a polypeptide which is a member of the protein kinase family and is expressed in tissues affected by DM.

The work described herein makes available a method by which a nucleotide sequence, specifically a CTG triplet repeat, shown to be expanded in individuals affected with DM, has been identified in a sample obtained from an individual. The present method is used to identify individuals in whom the CTG triplet repeat is present in normal copy number and individuals in whom the CTG triplet repeat occurs in abnormally high copy number, as well as to further identify individuals likely to be minimally affected and individuals likely to be more severely affected. An important feature of this invention is that the number of repeats or the length of the repeat region may be used to predict the severity of DM of the individual.

The work described herein also makes available a transcription unit or a DM gene, whose full genomic sequence has been determined by the Applicants, and which is likely to have an important role in the pathophysiology of DM. As shown herein, the mRNA which includes in its 3' untranslated region the transcribed CTG triplet repeat, encodes a protein kinase. It is reasonable to expect that amplification of the CTG triplet repeat affects the function of the DM gene, such as by causing a loss of expression of the allele carrying the expanded repeat or by causing a gain of function in the DM gene (e.g., deletion or inactivation of a binding site for a negative control element), or affects the function of neighboring genes. Alternatively, it is reasonable to expect that amplification of the CTG triplet repeat acts through a direct effect of DM transcripts carrying expanded repeats on nuclear structures or elements which affect control or modulate transcription or other critical cellular processes. Amplification of the CTG triplet repeat could also affect DNA tertiary structure or chromatin assembly and regulation.

The protein kinase encoded by the DM gene can be used as the basis for a method of identifying and treating individuals affected by DM, since the mRNA is expressed in tissues affected by DM. The presence or absence, and location, as well as the level of expression, of the protein kinase can be determined in tissues using, for example, polyclonal or monoclonal antibodies which recognize (bind) the protein kinase. Alternatively, the DM gene or mRNA can be detected and/or quantitated using DNA/RNA probes described herein and art-recognized hybridization techniques.

The work described herein also makes it possible to alter the amount of or redistribute the protein kinase, particularly in tissues affected by MD and, thus, change its effects on cells and its role in the pathophysiology of DM.

BRIEF DESCRIPTION OF THE DRAWINGS

FIGS. 5A–5B is the nucleotide (SEQ ID NO:8) and the deduced amino acid sequence (SEQ ID NO:9) of cDNA C28.

FIGS. 6A–6J is the nucleotide sequence of the DM gene, (SEQ ID NO:10) including the deduced amino acid sequence (SEQ ID NO:11). The sequences of the intron/exon boundaries have been determined and are indicated by the XXX sites located within the sequence.

FIGS. 8A and 8B is the nucleotide sequence of cDNA which contains an expanded trinucleotide repeat (SEQ ID NO:12).

DETAILED DESCRIPTION OF THE INVENTION

Figure 1A:
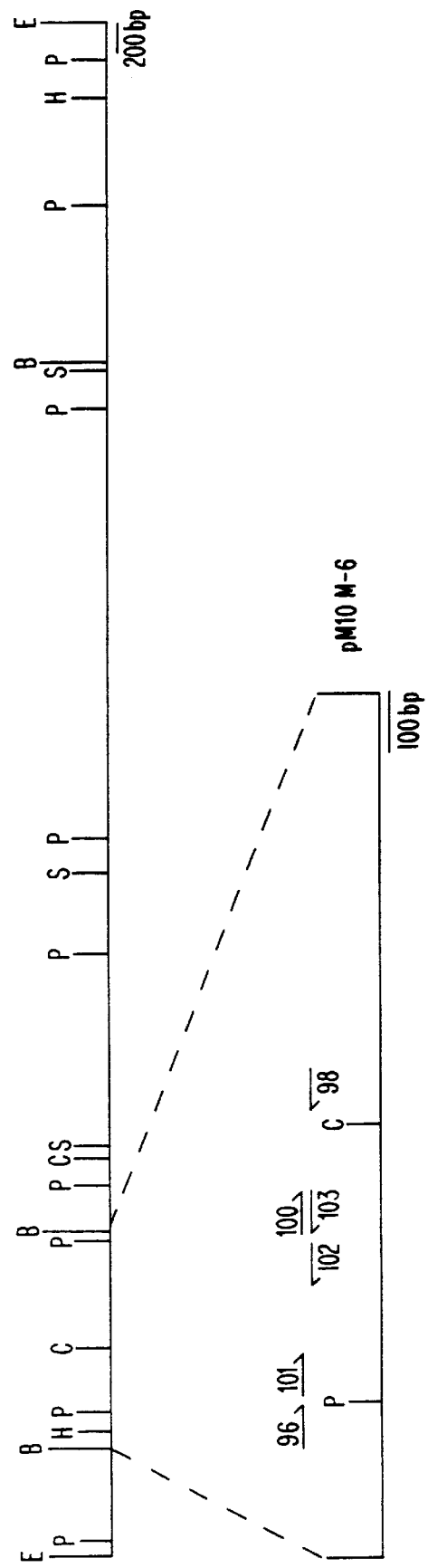
FIG. 1 is a restriction map of the 10 Kb EcoRI fragment that undergoes expansion in myotonic dystrophy patients. Restriction sites for BamHI(B), EcoRI(E), HincII(C), HindIII(H), PstI(P) and SacI(S) are indicated. The subcloned 1.4 Kb BamHI fragment (pMIOM-6) is shown enlarged with the PstI and the HincII sites, which flank the expanded region. The positions of PCR primers 96 (SEQ ID NO:1), 98 (SEQ ID NO:2), 100 (SEQ ID NO:3), 101 (SEQ ID NO:4), 102 (SEQ ID NO:5) and 103 (SEQ ID NO:6) and the sequence between primers 101 and 102 (SEQ ID NO:7) respectively are shown.

As described herein, the techniques of positional cloning have been used in order to identify the gene responsible for DM. This has resulted in two key findings, which are also described herein. First, a CTG triplet repeat whose copy number (number of repeats) is greater in affected individuals than in unaffected individuals and correlates with phenotypic severity has been identified. Second, the CTG repeat has been shown to be present in DNA which encodes a polypeptide with strong amino acid homology to members of the protein kinase family and is expressed in many of the tissues affected in DM.

The population may be divided into two distinct groups: those individuals who have fewer than approximately 50 repeats and are unaffected and those who have approximately 50 or more repeats and are affected. The number of repeats of the 3-base sequence is the underlying genetic difference between DM patients and normal individuals. Although it is usually the case in genetic inheritance that DNA sequences are passed from parents to offspring in an essentially unchanged form, this is not true of this particular sequence in DM families. In most cases the number of repeats increases on transmission from an affected parent to the affected offspring. This increase correlates with an increasing severity of symptoms, and earlier age-at-onset, in successive generations of a DM family.

These observations are based on extensive studies done by Applicants on two populations (Group A and Group B) involving hundreds of normal and DM samples in each population. The populations were analyzed as separate units although there was considerable overlap of samples.

Unaffected individuals, minimally affected individuals and severely affected individuals were tested for the presence of the CTG triplet. In a first study (Group A), the modal number of CTG triplet repeats in 282 unaffected individuals tested has been shown to be 5, with the largest number being 27. In a second study, (Group B), the largest number of CTG triplet repeats in 300 unaffected individuals was 40. In contrast, individuals minimally affected by DM have been shown to have at least approximately 50 CTG triplet repeats and more severely affected individuals have been shown to have even greater numbers of copies (e.g., expansion of the repeat-containing sequence by as much as several Kb pairs). The protein kinase polypeptide has been shown to be highly expressed in heart, expressed to a lesser extent in muscle and also expressed in brain.

The present work provides a nucleotide sequence, comprising:
(a) isolated DNA derived from human chromsome 19 including a variable number of repeats of the three-base unit CTG or its complement, wherein said number is greater than approximately 50 in individuals affected by myotonic dystrophy;
(b) isolated DNA which hybridizes under standard conditions to said first mentioned sequence over a region containing said variable number of repeats;
(c) isolated RNA transcribed from or corresponding to either of said aforementioned DNA sequences, or (d) a fragment containing one of said sequences.

The term "nucleotide sequence" or "nucleic acid sequence" refers to a polynucleotide such as a RNA or DNA molecule (the DNA may be single stranded or double stranded) along with any nucleotide analogues or other molecules that may be present in the sequence and that do not prevent performance of the present invention.

In particular, the present invention comprises DNA as shown in FIGS. 5A and 5B (SEQ ID NO:8), 6A–6J (SEQ ID NO:10) and 8A–8B (SEQ ID NO:12), their complementary strands and nucleic acid (both DNA and RNA) sequences that are substantially complementary to the nucleic acid sequences shown in those figures. A substantially complementary sequence is defined herein as a DNA or RNA sequence, for example, SEQ ID NO:10, which is sufficiently complementary to hybridize to SEQ ID NO:10 under conditions of high stringency as known to those of skill in the art. See, Ausubel et al. (1994) *Current Protocols in Molecular Biology,* Suppl. 26, John Wiley & Sons, Inc., New York, N.Y. For example, non-complementary bases or longer or shorter sequences can be interspersed in the complementary sequence provided the sequence has sufficient complementarity to SEQ ID NO:10 to hybridize therewith.

In another aspect, this invention provides a nucleic acid hybridization probe useful for determining the number of repeats of said three-base unit in a sample nucleic acid sequence as defined above, said probe including a nucleotide sequence capable of hybridizing to said sample nucleotide sequence, its complement or to a fragment of either of these. The nucleic acid probes of the present invention can comprise a fragment of a nucleotide sequence for example, a fragment of SEQ ID NO:8, SEQ ID NO:10 or SEQ ID NO:12, or their complements. To be useful as a probe the fragment must be of sufficient length and sequence specificity to hybridize to SEQ ID NO:8, SEQ ID NO:10 or SEQ ID NO:12 or their complements in a detectable manner. The criteria for selecting fragments suitable for use as hybridization probes are known to those of skill in the art. The nucleic acid probes can be detectably labeled, also as known to those of skill in the art.

Based on the work described herein, a method of determining in DNA obtained from an individual, the copy number of the CTG triplet repeat which has been shown to be increased or expanded in DNA of individuals affected with muscular dystrophy is available. Thus, a method of determining whether an individual is affected or is likely to be affected with myotonic dystrophy is also available. In the method, DNA is obtained from an individual to be assessed and the copy number of CTG triplet repeats on chromosome 19 DNA is determined. If the copy number of CTG triplet repeats is at least approximately 40 and typically at least 50, the greater the liklihood the individual will be affected with myotonic dystrophy. The presence of approximately 50 CTG triplet repeats is an indication that the individual is or will be minimally affected; the presence of a greater number of repeats is an indication that the individual is or will be more severely affected. The greater the number of CTG repeats, the greater the severity of myotonic dystrophy. Congenitally-affected individuals average about 1500–2000 CTG repeats but can vary considerably. Wieringa, Bé (1994) *Human Mol. Genetics,* 3:1–7. In this method, DNA can be obtained from a variety of tissues (e.g., blood, muscle, skin), either prenatally or postnatally.

The present work also provides a method of determining whether an individual is likely to be affected with myotonic dystrophy by determining the level of expression or distribution of the protein kinase encoded by the DNA of FIG. 5A–5B (SEQ ID NO:8); FIG. 6A–6J (SEQ ID NO:10) or FIG. 8A–8B (SEQ IN NO:12) (or a protein kinase having a substantially equivalent amino acid sequence), particularly in tissues affected by myotonic dystrophy (e.g., heart, brain and muscle) or in fibroblasts obtained from the skin, or in blood or serum. The term "substantially equivalent amino acid sequence" is defined herein to mean an amino acid sequence that differs, for example, from SEQ ID NO:11 (the amino acid sequence encoded by the DNA sequence, SEQ ID NO:10) by a replacement, an insertion or a deletion of at least one amino acid residue, yet maintains the biological activity of SEQ ID NO:11. These differences are also referred to herein as "silent" amino acid residue changes. In this method a tissue sample, for example, fibroblasts obtained from skin, to be analyzed is obtained from an individual to be assessed for the likelihood he or she will be or is affected with myotonic dystrophy. For example, amount of expression or distribution of the protein kinase can be determined through the use of an antibody specific for (one which binds) the protein kinase described herein. The antibody used can be polyclonal or monoclonal and is contacted with the tissue to be assessed, after the tissue has been processed or treated to render the protein kinase (if present) available for binding by the antibody. Binding of the antibody to a component of the tissue sample is indicative of the presence of the protein kinase and, thus, the amount or distribution of the enzyme can be measured to determine the likelihood the individual will be or is affected with myotonic dystrophy.

In many instances, the antibody can be labeled or a second antibody that binds to the first antibody can be labeled by some physical or chemical means. The label may be an enzyme which is assayed by the addition of a substrate which upon reaction releases an ultraviolet or visible light-absorbing product or it can be a radioactive substance, a chromophore, or a fluorochrome.

The work described herein also makes available antibodies specific for (which bind to) the protein kinase encoded by the DNA sequence of FIG. 5A–5B, FIG. 6A–6J or FIG. 8A–8B, or an equivalent protein kinase (a protein kinase encoded by a substantially similar DNA sequence and/or having substantially the same amino acid sequence as those represented in FIG. 5A–5B, FIG. 6A–6J or FIG. 8A–8B.

The work described herein also makes it possible to develop methods of treating or preventing myotonic dystrophy. For example, it is now known that a protein kinase is expressed in tissues affected by myotonic dystrophy and that the mRNA is transcribed from the DM gene with expanded repeats. This mRNA may or may not be translated and, if translated, the product may be distributed abnormally in tissues affected by myotonic dystrophy. See, Krishan, L. T. et al., (1994) *J. Biol. Chem.,* 128:995–1002; Kislauskis, E. H. et al. (1993) *J. Biol. Chem.,* 123:165–172. The effects of the protein kinase can be altered (totally or partially) by administering to an individual affected with or likely to be affected with myotonic dystrophy a drug or pharmaceutical composition which interferes with the protein kinase activity, either directly or indirectly. For example, a drug which interferes with expression of the protein kinase (e.g., a nucleotide sequence which binds to the kinase-encoding sequence and prevents it from being transcribed/expressed) can be used. As a result, less protein kinase is produced than would otherwise be the case and its effects are reduced. Alternatively, a drug which destroys or otherwise inactivates or interferes with the activity of the protein kinase can be administered.

It is also reasonable to expect that the expansion of the CTG repeat in the 3' UTR (untranslated region) of the protein kinase gene plays a role in the pathophysiology of myotonic dystrophy, perhaps through an effect on the gene or a neighboring gene. See, Shaw, D. J. et al. (1993) *Genomics,* 18:673–679. The expansion of the CTG repeat may lead to a gain or loss of function in the gene. In either case, it is possible to interfere with the effect of the expanded CTG repeats in the DM gene, such as by cleaving the expanded region from the gene or otherwise inactivating it.

The present invention also provides a means of identifying and altering the effects of a protein kinase encoded by a chromosome 19 gene containing a CTG triplet repeat greater than approximately 50. Monoclonal or polyclonal antibodies which bind to kinase polypeptides or proteins can be useful in the diagnosis, prevention or treatment (therapy) of the conditions or diseases resulting from the activity, inactivity, or redistribution of protein kinases or polypeptides, or to alter a cellular process controlled or mediated by these proteins or polypeptides. Genetic diseases like myotonic dystrophy lend themselves to a neutralizing antibody approach because their specific target mediates a multitude of different activities in diverse tissues. Many types of therapeutic antibodies can be used. Mouse/human chimeric monoclonal antibodies, humanized antibodies, phage repertoires, antibody fragments and bifunctional antibodies, and the like may be utilized for in vivo human therapy.

Understanding the mechanism of this disease also provides a basis for producing highly specific pharmaceuticals useful in controlling the adverse effects of myotonic dystrophy or similar pathologies resulting from DNA containing greater than approximately 50 CTG triplet repeats on chromosome 19.

Compounds that control or overcome the effects of protein kinase encoded by the DM gene or other proteins, the expression of which is affected by the increased number of triplets, can be formulated into pharmaceutical compositions containing a pharmaceutically acceptable carrier and/or other excipients using conventional materials and means. They can be administered to an animal, either human or non-human, for therapy of a disease or condition resulting from the activity of the DM gene containing greater than approximately 50 CTG repeats or for alteration of a cellular process mediated or controlled by a protein kinase encoded by this gene or other protein activity affected by this gene. Administration may be by any conventional route (parenteral, oral, inhalation, and the like) using appropriate formulations, many of which are well known. The compounds can be employed in admixture with conventional excepients, i.e., pharmaceutically acceptable organic or inorganic carrier substances suitable for parenteral administration that do not deleteriously react with the active derivatives.

Suitable pharmaceutically acceptable carriers include, but are not limited to, water, salt solution, alcohols, gum arabic, vegetable oils, benzyl alcohols, polyethylene glycols, gelatine, carbohydrates (such as lactose, amylose or starch), magnesium stearate, talc, silicic acid, viscous paraffin, perfume oil, fatty acid esters, hydroxymethycellulose, polyvinyl pyrrolidone, etc. For parenteral application, particularly suitable are injectable, sterile solutions, preferably oily or aqueous solutions, as well as suspensions, emulsions, or implants, including suppositories.

It will be appreciated that the actual preferred amounts of active compound in a specific case will vary according to the specific compound being utilized, the particular compositions formulated, the mode of application, the particular situs of application, and the age of the individual being treated. Dosages for a given recipient will be determined on the basis of individual characteristics, such as body size, weight, age and the type and severity of the condition being treated.

The following is a description of the mapping of the DM region of chromosome 19, which is increased in size in DM; identification of the CTG triplet repeats on chromosome 19 and assessment of the number of repeats in normal and affected individuals; identification and characterization of genomic clones spanning the 10 kb fragment which is increased in size in DM; the cDNAs which were isolated from various libraries by probing with one of the genomic clones; and the full length DNA sequence of the DM gene.

Over the past few years, both genetic maps (Johnson, K. et al., *Am. J. Hum. Genet.* 46:1073–1082 (1990); Harley, H. G. et al., *Nature,* 355:545–546 (1991); Tsilfidis, C. et al. *Am. J. Hum. Genet.* 49:961–965 (1991)) and physical maps (Korneluk, R. G. et al., *Genomics* 5:596–604 (1989); Smeets, H. et al., *Am J. Hum. Genet.* 46:492–502 (1990); Brook, J. D. et al., *Hum. Genet.* 87:65–72 (1991); Brook, J. D. et al., *J. Med. Genet.* 26:84–88 (1991)) of the long arm of human chromosome 19 have been produced to localize the DM gene to band 19q13.3 between DNA markers ERCC1 and D19S51. Construction and analysis of radiation-reduced hybrids, as described herein, and YAC, cosmid, and phage libraries (Buxton, J. et al., *Nature* 355:547–548 (1992); Jansen, G. et al., *Nature* 332:276–281 (1992)) has allowed saturation mapping of the interval between these two markers. The DM region could be narrowed down further through linkage disequilibrium studies. Markers D19S63 and D19S95 are in strong linkage disequilibrium with DM (Harley, H. G. et al., *Hum. Genet.* 87:73–80 (1991), Harley H. G. et al., *Nature* 355:545–546 (1992)). No disequilibrium was observed for markers flanking these loci. Screening of phage libraries derived from the radiation reduced hybrid, 2F5 (produced as described in the Group A Exemplification) produced a series of overlapping phage clones that spanned the interval between D19S63 and D19S95.

This intensive search resulted in the identification of DNA markers adjacent to D19S95 that detect patient specific bands on Southern blots (Harley, H. G. et al., *Nature* 355:545–546 (1992); Buxton, J. et al., *Nature* 355:547–548 (1992); Aslandis, C. et al., *Nature* 355:548–551 (1992)). Probes pBBO.7 (Harley, H. G. et al., *Nature* 355:545–546 (1992) and cDNA 25 (Buxton, J. et al., *Nature* 355:547–548 (1992) identify the same EcoRI restriction fragment length polymorphism in the normal population, with alleles of 9 kb or 10 kb. In 43 of 53 unrelated affected individuals reported in these two studies, only one of the normal-sized alleles is present, plus an additional, larger, disease-specific band. This restriction fragment varies in length between patients, even between siblings within the same family. Furthermore, the size of the variable fragment increases in successive generations and shows a correlation between increased severity and earlier onset of the disease. The largest fragment detected is 15 kb, an increase of 5 kb over the normal size (Harley, H. G. et al., *Nature* 355:545–546 (1992).

In many individuals with fragments larger than 11 kb, a diffuse hybridization signal corresponding to a DNA fragment size greater than 11 kb is observed in a gel that otherwise gives tight DNA banding patterns, indicating that somatic mosaicism with respect to the precise extent of the increase in size of the DNA sequence within the EcoRI fragment has occurred. This situation is strikingly similar to that reported recently for the fragile-X syndrome, where variation in length of a CGG repeat results in genetic instability (Dietrich, A. et al., *Nucl. Acids Res.*

19:2567–2572 (1991); Fu, Y.-M., et al., *Cell* 67:1047–1058 (1991); Kremer, E. J. et al., *Science* 252:1711–1714 (1991); Oberle, I. et al., *Science* 252:1097–1102 (1991); Verkerk, A. J. et al., *Cell* 65:905–914 (1991); Yu, S. et al., *Science* 252:1179–1181 (1991)). In order to identify the mutation in DM, genomic clones spanning the 10 kb fragment that is increased in size in this disease were characterized in two studies, each of which includes affected and unaffected individuals as described supra. A CTG repeat sequence was identified that is highly polymorphic in the normal population and that undergoes huge expansion in DM patients.

In Group A, the modal number of repeats found in 282 normal alleles surveyed is 5 (48%), with the largest being 27. Minimally affected DM patients have at least approximately 50 copies. The CTG repeat is transcribed and is found at a position 500 bp from the poly(A) tract of an mRNA expressed in many of the tissues affected in DM. The RNA in which the repeat resides encodes a polypeptide with strong amino acid homology to members of the protein kinase gene family.

In Group B, the number of repeats in DM patients is found to exceed 50 and unaffected individuals have less than 40 repeats. The observations of Group B are based on samples involving 100 DM families and 200 normal individuals. (It should be noted that although the Examples describe the analysis of two populations of DM patients, considerable overlap of patient samples between the two groups existed.) The work which resulted in the findings described above is described in detail in the following sections. The experimental procedures used are described in a subsequent section.

Fine Mapping of the Region Amplified in DM Patients

A series of phage clones derived from libraries of radiation-reduced hybrid 2F5 (see the Group A Exemplification) were used to span the interval between D19S63 and D19S95, the loci in linkage disequilibrium with DM. Intensive screening of this interval led to the identification of clones λM1OM (detected by hybridization with cDNA 25 (Buxton et al., *Nature* 355:547–548 (1992)) and λM8L and λSM2 (which contain clone pBBO.7 (Harley et al., *Hum. Genet.* 87:73–80 (1992)). These clones span the 10 kb EcoRI fragment that is increased in size in DM patients. FIG. 1 shows a detailed restriction map of this interval. Sites for BamHI, HincII, HindIII, PstI, and SacI are marked. Single-copy probes mapping within this EcoRI fragment were hybridized to DNA from patient and normal individuals digested with a series of restriction enzymes.

GROUP A

Figure 2:
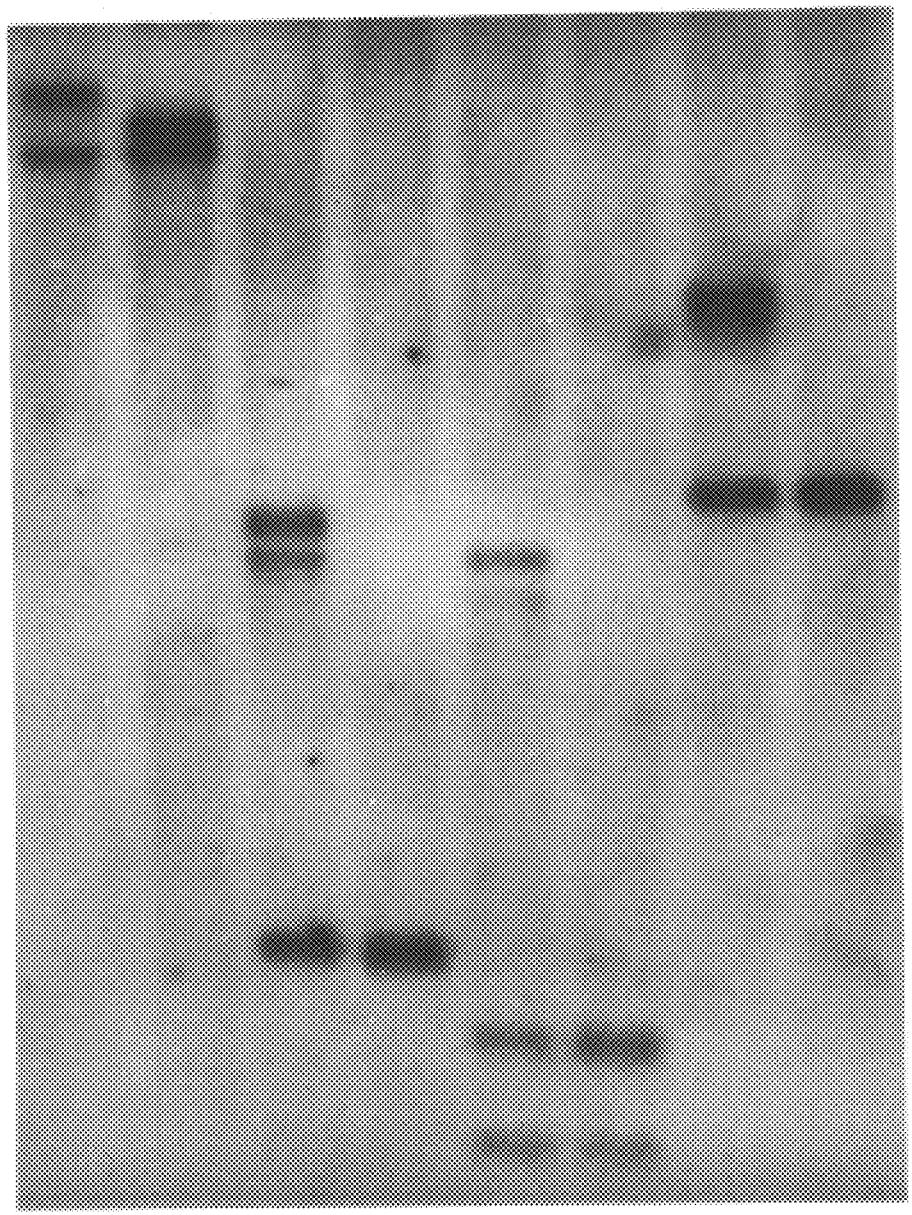
FIG. 2 shows results of Southern blot analysis of the DNA fragment which is expanded in DM. DNA from a DM patient (DM) and an unaffected individual (N) of Group A, digested with EcoRI, BamHI, PstI and SacI and hybridized with pMIOM-6 shows an increased band in the DM lane with all enzymes.

FIG. 2 shows the result of hybridization with a single-copy probe as described above. The normal control is heterozygous for an EcoRI RFLP. As previously reported, a patient-specific EcoRI band, larger in size than either normal allele, is observed in the DNA of the DM patient (Harley et al., 1992; Buxton et al., 1992). Digestion with BamHI, PstI, and SacI each revealed patient-specific bands. The smallest region containing the expanded sequence that could be established by hybridization was a 475 bp PstI-HincII fragment contained within the 1.4 kb BamHI fragment (pM10M-6) shown in FIG. 1. Part of this fragment was sequenced to make primers for polymerase chain reaction (PCR) analysis. Amplification by PCR between oligos 98 and 100 produced single bands that were identical in size in patient, normal and pM10M-6 lanes when visualized on ethidium-stained agarose gels. In contrast, PCR using oligos 96 (SEQ ID NO:1) and 103 (SEQ ID NO:6) produced two bands in a normal human sample, a single band in DM DNA and a single band in pM10M-6 that was smaller than any of the other bands. Analysis of the sequence derived from pM10M-6 between oligos 96 (SEQ ID NO:1) and 103 (SEQ ID NO:6) revealed tandem repeats of the trinucleotide CTG. Two other oligos, 101 (SEQ ID NO:4) and 102 (SEQ ID NO:5), which more closely flank this triplet repeat, were tested using PCR. These produced similar but more striking band size differences than with oligos 96 and 103 because of the smaller PCR product. The sequence of pM10M-6 between oligos 101 (SEQ ID NO:4) and 102 (SEQ ID NO:5) is shown in FIG. 1.

Variability of the CTG Repeat in the Normal Population

In order to examine length variability of the PCR fragment produced with oligos 101 (SEQ ID NO:4) and 102 (SEQ ID NO:5) in the normal population, radio-labeled products obtained from a series of normal individuals were analyzed on sequencing gels. The majority of individuals are heterozygous at this locus. Interestingly, shadow bands occurred in positions indicating that they differed by three bases from the major bands.

To confirm that this variability of length is due to different numbers of the triplet repeat, the PCR products from two normal heterozygous individuals were cloned and sequenced. From one individual, six clones were analyzed; three contained 12 copies of the CTG repeat, two contained 17 repeats, and one had 18 repeats (the variation between clones with 17 and 18 repeats may be an artifact of stuttering during PCR). In the second individual, two clones were sequenced and contained 5 and 11 copies of the repeat. These repeat lengths are consistent with the size of bands from these individuals determined by analysis of labeled PCR products on sequencing gels. In all clones analyzed, the sequence flanking the repeat was identical to that derived from pM10M-6, with the exception of two point mutations, which differed between clones and which may be due to errors by Taq polymerase.

Figure 3:
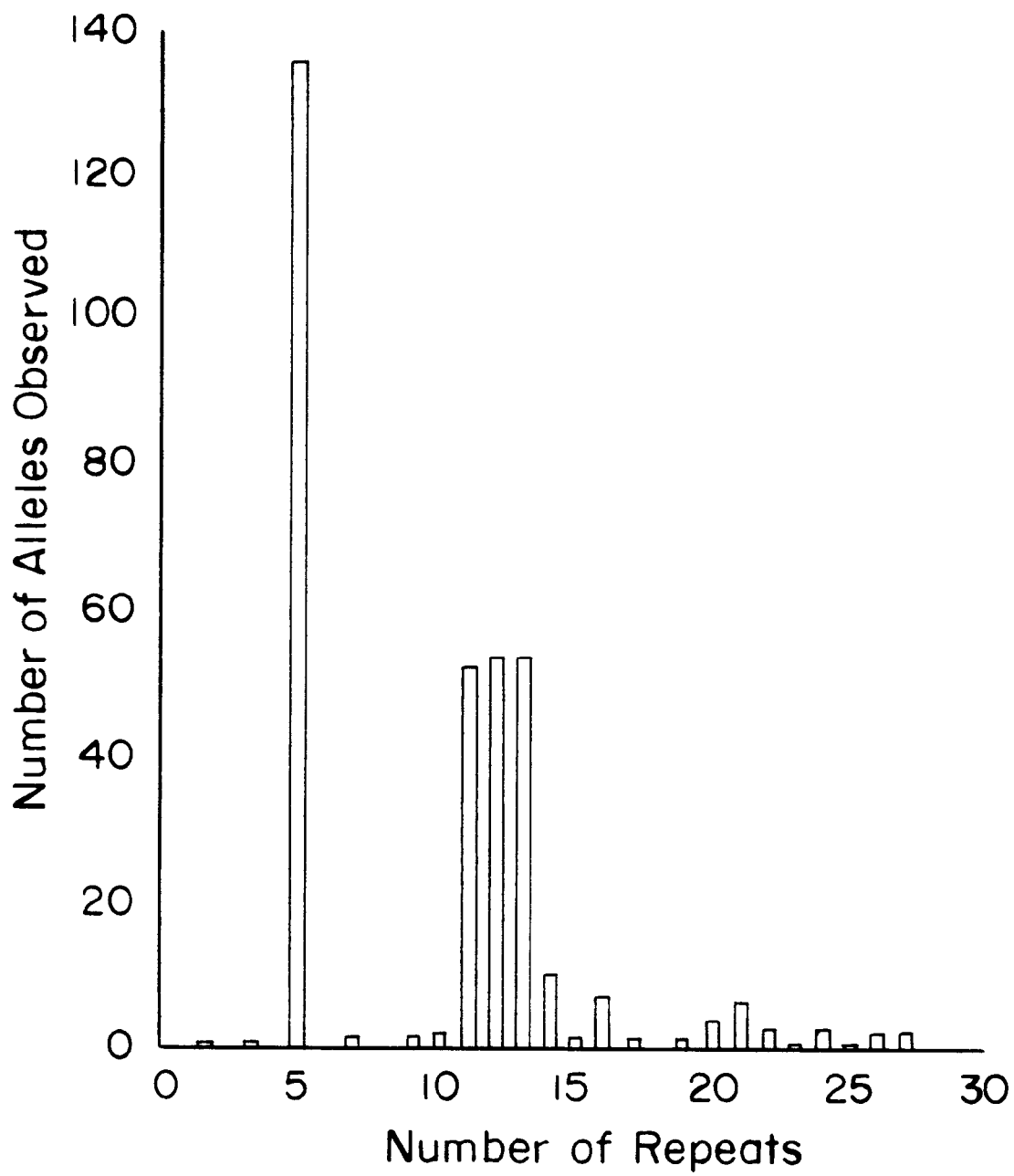
FIG. 3 is a graphic representation of the distribution of repeat lengths in the normal population (n=282) of Group A.

The variation in repeat length was analyzed in 282 individuals, and the distribution of repeats in the normal population is shown in FIG. 3. Alleles were sized against sequenced standards and sequencing ladders. Over 40% of alleles analyzed had 5 repeats. No alleles were observed with 6 or 8 triplets, and only single examples of 7 and 9 were found. The majority of repeats were in the 10–16 interval, with the highest being 27. Normal Mendelian inheritance was demonstrated for 20 meioses in two CEPH pedigrees.

Variability of the CTG Repeat in DM Patients

Initial attempts to characterize the variable region in patients led to the observation that the DM sample tested by PCR assay produced a single band. To establish whether the single band was specific to this sample or whether it reflected something common to all patients, we analyzed by PCR 12 unrelated DM samples. PCR products were visualized on ethidium-stained gels. In all cases a single band from the normal size range (<200 bp) was present. In one sample (DMH9) a faint diffused band was observed above 360 bp on ethidium-stained gel. This patient was not severely affected and did not show signs of the disorder until age 45. In order to determine the nature of the larger fragment in patient DMH9, the PCR product from this individual was cloned and sequenced. In excess of 80 CTG repeats were present. It was not possible to read beyond the CTG triplet; however, sequencing from either side of the repeat revealed that the flanking DNA was intact and had the same sequence as pM10M-6.

A single band was observed in PCR analysis of DNA from 11 of 12 patients, who had increases in Southern blot bands of 2 kb or more. The 12th patient, an individual who had later onset of the disorder, produced a faint upper band on PCR analysis. This suggested that in the other 11 patients it had been impossible to amplify their second allele because of the extent of the amplified CTG repeat. In order to identify additional individuals likely to contain expanded CTG repeats that could be successfully identified by PCR, we focused on other mildly affected individuals. Three pairs of grandparents were selected from DM pedigrees in which it was difficult to decide, on clinical grounds, which was the affected individual. In each case, one of the pair had cataracts. PCR products analyzed on ethidium-stained gels showed that one individual from each pair had two alleles in the normal range, whereas the other grandparent (in each case, the one with cataracts) had one band in the normal range in addition to a second diffuse band at about 250 bp. For accurate sizing of this larger band labeled PCR products were analyzed on sequencing gels. Although unrelated, these two individuals had very similar larger bands (corresponding to 50–55 repeats). The larger allele was amplified using PCR and cloned and sequenced, in order to determine whether the increased fragment size in these patients is due entirely to the expansion of the CTG repeat. Six clones were analyzed from one patient (DMH6): four contained 52 repeats, one had 54 repeats, and one had 57 repeats. Analysis of five clones from patient DMH1 revealed two with 50 repeats, two with 52 repeats, and one had 61 repeats. In all clones the sequence of the DNA flanking the repeat was the same as that derived from pM10M-6. The only difference was in the length of the triplet repeat. The different CTG lengths observed in different clones from the same individual may reflect somatic mosaicism or stuttering during the PCR reaction.

Figure 4:
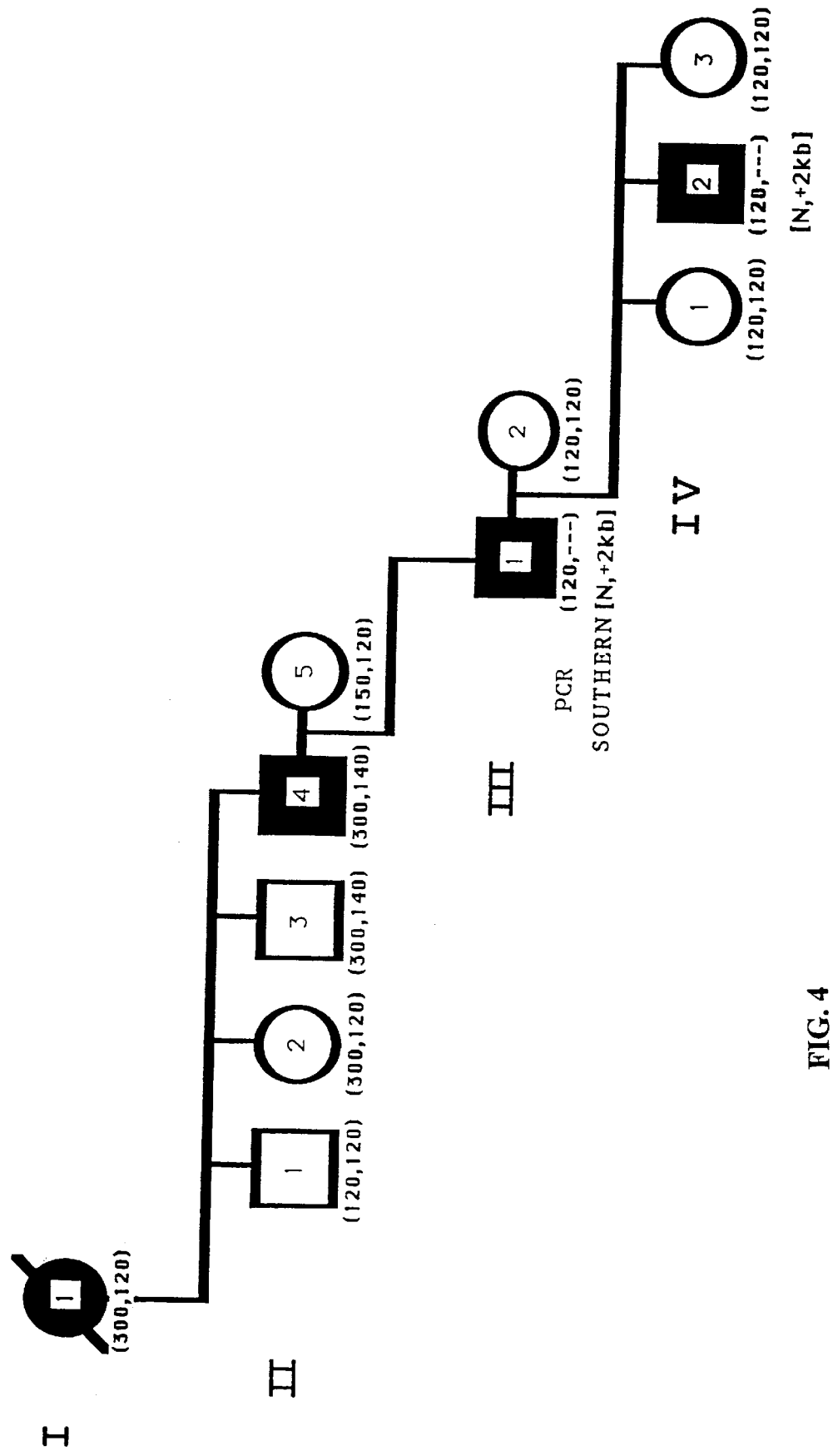
FIG. 4 is the pedigree of a myotonic dystrophy family of Group A with their genotypes at the DM locus.

A DM family that shows increased severity of disease in successive generations is shown in FIG. 4. A band of approximately 300 bp is observed in the PCR product of four family members in the first two generations shown in the pedigree. This result demonstrates that a CTG repeat unit of approximately 60 repeats can be transmitted from one generation to the next without an obligatory expansion. Individuals in the first two generations had mild symptoms such as cataracts or were apparently asymptomatic. However, individuals in the third and fourth generations of the family showed severe symptoms of DM. These individuals showed only a single PCR band within the normal range. Southern blotting analysis confirmed that, for these individuals, as for most other severely affected DM patients, a dramatic expansion in allele size has occurred to increase the repeat size beyond that which can be detected by PCR analysis.

The CTG Repeat Is Transcribed

The triplet repeat sequences amplified in fragile-X syndrome and X-linked spinal and bulbar muscular atrophy (SBMA) are expressed in mRNAs. To test whether the CTG repeat amplified in DM might be within a gene, clone pM10M-6 was hybridized to a Southern blot of DNA from different species. Results showed that DNA sequences contained within this clone are strongly conserved, suggestive of a transcribed sequence. pM10M-6 was used to screen cDNA libraries derived from several different sources, including adult frontal cortex, substantia nigra, fetal muscle and fetal brain. A total of $10^6$ clones were screened from these libraries and 110 positives were identified. Twenty were purified and six, from different libraries, were selected for further analysis. These clones were designated C28, C31, C34, C35, C39 and C85. The insert size of each clone and the library from which it was derived are: C28 (frontal cortex), 2.5 kb; C31 (frontal cortex), 2.1 kb; C34 (substantia nigra), 1.7 kb; C35 (fetal brain), 1.7 kb; C39 (frontal cortex), 2.7 kb; C85 (fetal muscle), 2.8 kb. All six clones were hybridized to a panel of hybrid cell lines to confirm that they were from the expected region of chromosome 19. They were also mapped to filters of digested genomic phage clones λM10M and λM8L (which span the 10 kb EcoRI fragment amplified in patients) to determine how much genomic DNA they cover. cDNAs C28 and C85 each span at least 10 kb of genomic DNA. Clone C39 was chimeric at the 5' end, whereas the others mapped as expected. Clones C28, C34 and C35 were completely sequenced and clone C85 was partially sequenced. All clones contained the CTG repeat, and this varied in length between clones. Clones C28, C34, C35, and C85 contained 11, 5, 12, and 13 triplets, respectively. Comparison of the cDNAs with the genomic clones indicates that the gene is transcribed in the orientation telomere-to-centromere and that the CTG triplet is on the coding strand.

Results of Northern blot analysis with C28 showed that the full-length transcript is between 3.0 and 3.3 kb in length and is highly expressed in heart and to a lesser extent in muscle. Prolonged autoradiographic exposure indicates that this transcript is also expressed in brain, consistent with the identification of cDNAs from this tissue. The sequence of C28 is shown in FIG. 5A–5B. This clone contains a complete 3' terminus, which includes the polyadenylation addition signal AAUAAA. The largest predicted open reading frame extends from the beginning of the sequence to position 1747 with a coding capacity of 582 amino acids. The C28 sequence was compared to the nonredundant sequence database, which combines all available protein databases. This sequence search revealed homology to the cyclic AMP-dependent protein kinases. The highest score was to the protein kinase TKR-YKR from *Saccharomzyces cerevisiae*. The 11 protein kinase domains are found within the first 300 residues of deduced amino acid sequence. Beyond the kinase domain, some slight homology to the chicken myosin heavy chain was observed.

The disease, myotonic dystrophy, shows a clear autosomal dominant pattern of inheritance. However, there are several aspects of this disorder that are particularly challenging to explain from a molecular genetic perspective. First, there is the considerable variability of phenotype between affected individuals, even within the same family. Second, there is an association of DM with specific haplotypes in the population (Harley, H. G. et al., *Hum. Genet.* 87:73–80 (1991) indicating that most cases have resulted from a small number of genetic events. Third, there is the multi-systemic nature of the phenotype. Fourth, there is an apparent increase in severity of symptoms and reduction in age at onset that is observed during transmission of the gene within families.

Several molecular genetic features of DM appear to be directly comparable to fragile-X syndrome. In fragile-X syndrome, increasing allele size at the FMR-1 locus, measured by Southern hybridization, is due to expansion of a CGG repeat at the 5' end of the FMR-1 gene. Increased allele size correlated with the severity of disease (Fu, Y.-M. et al. *Cell* 67:1047–1058 (1991). The extent of fragment size increase in DM also shows a clear correlation with increased severity and age at onset of the disease (Harley, H. G. et al., *Nature* 355:545–546 (1992); Buxton, J. et al., *Nature* 355:547–548 (1992). The identification of a CTG repeat, which is highly variable in the normal population and which is greatly expanded in DM patients, extends the parallels between DM and fragile-X.

Analysis of cloned PCR products reveals that the increase in size of the PCR products observed in mildly and minimally affected DM patients is due entirely to increased number of the CTG repeats. The DNA flanking the repeat is intact in all clones examined. Two minimally affected patients, DMH1 and DMH6, had repeat lengths of 50 and 62 CTGs, respectively, whereas a slightly more severely affected patient, DMH9, had in excess of 80 repeats. PCR analysis of the most severely affected patients reveals only a single band, which is in the normal size range. In these individuals the expanded allele cannot easily be visualized by PCR assay. Thus, as with fragile-X, phenotypic severity correlates with the number of repeats.

Other similarities and differences between DM and fragile-X are noteworthy. In fragile-X, individuals are categorized as normal premutation or full mutation on the basis of CGG repeat number (Fu, Y.-M et al., *Cell* 57:1047–1058 (1991)). Transmissions of 46 repeats and below are within the normal range and are stable. The transition from stability to instability occurs within the 46–52 repeat range. Permutations showing no phenotypic effect range from 52 to 200 repeats and are meiotically unstable. For myotonic dystrophy there is, as yet, no clear classification of premutation. However, it seems likely that minimally affected individuals could go undiagnosed, were it not for the appearance of a more severely affected individual in a subsequent generation. This point is further illustrated in FIG. 4, in which two siblings appeared normal on clinical examination at ages 64 and 61, yet showed the same upper allele as their mother, who lived to age 89 and who did not show myotonia but did have cataracts. These minimally affected individuals may be comparable to the premutational state seen in fragile-X.

The molecular mechanisms that determine the stability during inheritance of DM alleles is unclear at present. There is considerable variability at this locus in the normal population: over 75% of normal individuals are heterozygous. The largest allele observed had 27 repeats. The most common allele in the population, 5 repeats, is found at a frequency of 0.48. Analysis of repeat length in 141 individuals revealed no alleles with fewer than 5 copies of the repeat. Furthermore, only two alleles were found in the 6–9 repeat range. Replication of the 5 repeat allele appears to be stable. Duplication or triplication with subsequent slippage during DNA replication (Jeffreys, et al., *Nature* 332:278–281 (1988)) may account for the generation of other alleles. Unequal crossing over would seem to be unlikely as the mechanism generating allelic diversity, in view of the shortage of alleles between 5 and 10 repeats. Clearly, further study of the mechanisms that underlie variation in repeat length at the DM locus will be of great interest. In addition, it will be important to determine the extent of tissue mosaicism in the expansion of the CTG repeat. Such mosaicism could have a significant impact on clinical phenotype.

One of the families documented by Fu, et al., appears to represent a fragile-X premutation segregating in the normal population, which has yet to undergo expansion to the full mutation (Fu, Y.-M. et al., *Cell* 57:1047–1058 (1991)).

It is unclear in fragile-X whether a new mutation is a frequent event. It seems quite possible, however, that transition from a large allele in the normal population to premutation allele in fragile-X could occur by the same mechanism that generates diversity amongst alleles in the normal size range (Fu, Y-M et al., *Cell* 57:1047–1058 (1991)). Thus, large alleles in the normal population and fragile-X permutations would represent a continuum across a stability threshold, with the fragile-X phenotype generated by multiple independent events. At the DM locus, however, two observations suggest that expansion of the CTG repeat to a clinically significant level is likely to occur only in a specific population subgroup.

First, there is clear evidence in heterogeneous populations of linkage disequilibrium between DM and polymorphisms at "nearby" loci (Harley, H. G. et al., *Hum. Genet.* 87:73–80 (1991); Harley, H. G. et al., *Nature* 355:545–546 (1992)). This implies either that there are few mutations, possibly a single ancestral event, or that specific nearby polymorphisms predispose to the generation of DM mutations. It is difficult to envisage a mechanism by which multiple polymorphisms at distances of up to 70 kb (in the case of D19S63) from the CTG repeat could predispose to DM. On the other hand, if there are very few, if any, new mutations, some mechanism must maintain the disease allele in the population, particularly in view of the genetic endpoint represented by severely affected individuals. Thus, there may be a large unrecognized pool of individuals in the population who carry and transmit the DM premutation with little, if any, phenotypic effect. Extensive studies of normal population (possible focusing on individuals with cataracts) will be necessary to test this possibility.

Second, the distribution of CTG repeat alleles is quite distinct in the normal population and in DM patients. In DM the smallest number of CTG repeats observed is 50, almost double the largest number of repeats seen in the normal population of Group A. It is possible that a doubling or tripling in repeat number is the ancestral event that predisposes an allele at the DM locus to further expansion into an allele associated with the complete disease phenotype.

While it is certainly possible that amplification of the CTG affects the expression of several transcription units in the immediate vicinity of the repeat, it seems very likely that the transcription unit we have identified in this study plays an important role in the pathophysiology of DM. The mechanism through which expansion of the CTG repeat affects the function of the DM gene remains to be elucidated. Since DM is a dominantly inherited disorder, mutant alleles must exert an effect in the presence of a normal allele. There are a number of possible ways in which an amplified sequence in the 3' UTR of a gene could exert an effect on the function of that gene. One possibility is that, analogous to fragile-X, the expansion of the CTG repeat causes a loss of expression of the allele carrying the expanded repeat. If this is the case, then the DM gene must indeed be extremely sensitive to gene dosage, since gene expression levels in the presence of a normal allele can range only between 50% and 100% of normal. Genomic imprinting cannot be invoked to increase this range too much further, since DM can be inherited from either the father or the mother, with quite severe symptoms. Alternatively, the expansion of the CTG repeat may lead to a gain of function in the DM gene. Gain-of-function mutations in the 3' UTR of the fem-3 and lin-14 genes of *Caenorhabditis elegans* have recently been demonstrated (Ahringer, J. and J. Kimble, *Nature* 349:346–348 (1991); Wightman, B. et al., *Gene Dev.* 5:1813–1824 (1991)). In both cases, deletion or inactivation of a binding site for a negative control element is thought to result in unregulated activity of these genes. Amplification of the CTG repeat in DM may be producing a similar effect. However, only one study has reported an increase in protein kinase associated with DM cells and tissues. Sabouri et al., *Nature Genetics* 4:233–238. Others suggest that primary transcripts of MRNA in the brain, heart and muscle may be subject to tissue specific alternative splicing. Shaw, (1993) supra.

The similarity of the DM gene to members of the protein kinase family, in particular cAMP-dependent protein kinase (cAPK), opens a broad range of physiological questions that should be directly tested. cAPKs (Hunter, T., *Meth. Enzymol.* 200:3–37 (1991)) are known to modulate the activity of excitable cells by phosphorylation of ion channels, exert control of glycogen and lipid metabolism through cascades of enzyme phosphorylation, and modify gene expression (Yamamoto, K. K. et al., *Nature* 334:494–498 (1988); Foulkes, N. S. et al., *Cell* 54:739–749 (1991)). Abnormalities in function or regulation of such a molecule fit well with the diverse phenotypic effects exhibited by DM patients.

In a further aspect, this invention provides a method of DM risk diagnosis which comprises directly or indirectly observing monitoring or determining the number of repeats of the base sequence CTG or its complement in the DNA from chromosome 19, or the number of repeats of the equivalent three-base unit in RNA transcribed from or corresponding to said DNA sequence, or observing monitoring or determining the length of the region containing said repeats.

This invention provides nucleic acid hybridization probes useful for determining the number of repeats of three-base units in a sample nucleotide sequence as defined above, the probes including a nucleotide sequence capable of hybridizing to the sample sequence, or its complementary sequence or to a fragment of either of these, the probes each having associated therewith a detectable label.

This method of DM risk diagnosis preferably involves hybridizing a sample of genomic DNA or RNA from an individual with one or more probes as defined above, the sample preferably initially being exposed to a restriction enzyme before hybridization with the probe or probes.

Suitable restriction enzymes are EcoRI, EcoRV, PstI and PvuII, although many other enzymes which, with the appropriate probe, provide fragments which differ in length between DM patients and unaffected adults, may be used.

The invention also extends to primers for use in a nucleic acid amplification technique (for example the PCR or polymerase chain reaction) for amplifying at least the variable repeat region of a nucleotide sequence as defined above. The primers preferably comprise first and second oligonucleotides closely flanking said repeat region (e.g. each spaced between about 5 and 75 bases therefrom). Said first and second oligonucleotides preferably each comprise respective sequences of from 8 to 32 bases and in one embodiment are substantially as identified by primer references 101 and 102 in FIG. 1 (SEQ ID NO:4 and SEQ ID NO:5, respectively), or complements thereof.

In a further aspect, this invention provides a diagnostic kit for carrying out a method of DM risk diagnosis which involves hybridizing a sample of genomic DNA or RNA from an individual with one or more hybridization probes, wherein the kit includes a hybridization probe and one or more other components for carrying out the method, characterized in that said hybridization probe is as defined above, and optionally including PCR primers.

The techniques disclosed herein have the capability to distinguish between normal unaffected people and carriers of the DM gene, even when these cannot be diagnosed by clinical examination alone. This can be done by standard methods of DNA or RNA analysis, including Southern or Northern blotting and hybridization, and/or PCR (polymerase chain reaction). There is always a risk to gene carriers that their offspring may be severely affected, and therefore there is a demand from DM families for carrier detection by DNA or RNA testing. When a pregnancy at risk for DM is already under way, the family will often request prenatal diagnosis of the fetus by means of chorionic villus sampling or amniocentesis and DNA analysis, following which a decision may be made regarding termination or continuation. At present the DNA diagnosis is done indirectly using DNA sequences that are not themselves part of the DM gene; this is often technically unsatisfactory and requires the cooperation of other family members than those directly involved. Furthermore, it gives no indication of the severity of the symptoms, only that the disease gene is or is not present. The techniques disclosed herein will overcome these limitations since they allow diagnosis of the presence of the disease gene in a sample of DNA or RNA from just the person in question, without the need for a full family analysis. This increases the speed of the procedure (an important consideration when a pregnancy is ongoing) and reduces the risk of misdiagnosis considerably. More significantly, these techniques will enable a prediction to be made concerning the severity of the disease in the person or pregnancy at risk. Because DM is a highly variable condition, ranging from a trivial adult complaint to a potentially lethal congenital illness, it is important for the family and their counsellors to know how severe a form is involved, so that informed choices may be made.

The present invention will now be illustrated by the following examples, which further and more specifically illustrate the invention.

GROUP A EXEMPLIFICATION

EXAMPLE 1

Experimental Procedures

PCR Analysis

The PCR analysis was performed as follows. Reactions (10 μl) were set up using standard PCR conditions (50 mM KCl, 1.5 mM $MgCl_2$, 10 mM Tris [pH 8.3], 200 μM dNTPs, 1 μM of each primer, and 20 ng template DNA). For the radiolabeled experiments, oligo 101 (SEQ ID NO:4) was incubated for 30 min at 37° C. with T4 polynucleotide kinase (3μ) in 20 μl reaction with 50 mM Tris-HCl (pH 7.5). 10 mM $MgCl_2$, 5 mM dithiothreitol, 0.1 mM spermidine, and 1 μl of (λ32P) ATP (3000 ci/mmol). The PCR reaction was spiked with the labeled primer in a ratio of 30:1 unlabeled to labeled. PCR reactions were carried out on a Stratagene 96 well thermocycler. Cycling conditions were as follows: 1×(3 min, 94° C.), 35× (10s, 94° C.; 30s, 62° C.; 30s, 72° C.), 1× (5 min, 72° C.), 15° C. soak. Samples then were either loaded on agarose gels or were diluted 1:1 with sequencing buffer, denatured and loaded on 8% sequencing gels.

The sequences of oligos used in PCR reactions were as follows:

96, GGT GCG TGG AGG ATG GAA CAC GGA C (SEQ ID NO:1)

98, GCG TGC GAG TGG ACT AAC AAC AGC TG (SEQ ID NO:2)

100, CAC GCT CGG AGC GGT TGT GAA CTG G (SEQ ID NO:3)

101, CTT CCC AGG CCT GCA GTT TGC CCA TC (SEQ ID NO:4)

102, GAA CGG GGC TCG AAG GGT CCT TGT AGC (SEQ ID NO:5)

103, CCA GTT CAC AAC CGC TCC GAG CGT G (SEQ ID NO:6)

Genomic Digests and Southern Blots

Genomic DNAs were digested with restriction endonucleases PstI, SacI, EcoRI or BamHI (New England Biolabs) in 30 μl or 40 μl reactions with NE Buffer 10× according to the manufacturer's instructions. Digested DNAs were run on 0.8% agarose gels (FMC), denatured in 0.5M NaOH, 1.5M NaCl, neutralized in 1M Tris (ph 7.0), 1.5M NaCl and transferred to membranes, sold under the trademark ZETABIND (AMF), in 10× SSC.

Hybridizations

Hybridizations to both Northern and Southern blots were performed at 42° C. in 50% formamide with 5× SSC, 1× Denhardt's solution, 0.02M $NaPO_4$, 100 μg/ml single-stranded DNA, 10% dextran sulphate. DNA probes were labeled by random priming (Feinberg, A. P. and B. Vogelstein, *Biochem. Biophys. Res. Commun.* 111:47–54 (1983)).

Northern Blots

Total RNA was extracted from baboon tissue using the method of Auffray and Rougeon (1980) with modifications from Buckler et al. (1991). Poly(A) RNA was isolated from oligo(dT)-cellulose, and gels and Northern blots were set up as described in Buckler et al. (1991).

DNA Sequencing

Three parallel sequencing strategies were adopted. Much of the sequencing was carried out using a U.S. Biochemical sequence kit according to manufacturer's instructions on cDNA constructs. In general, vector oligonucleotides were used as primers, and in some cases, specific oligonucleotides were synthesized from deduced sequence.

cDNA Libraries

Four cDNA libraries were screened. Three, constructed in λZAP from frontal cortex, substantia nigre and fetal brain were kindly supplied by Dr. Marcy MacDonald. A total muscle library in λGT10 was kindly supplied by Dr. L. Kunkel (Koenig, et al., *Cell* 50:509–517 (1987)).

DNA Database Searching

DNA databases were searched on a digital VAX computer using the GCG (Genetics Computer Group) software package (Altschul, S. F. et al., *J. Mol. Biol.* 215:403–410 (1990)) and the BLAST network service (NIH NLM Basic Local Alignment Search Tool suite) from the National Center for Biotechnology Information.

Radiation Reduced Hybrids for the Myotonic Dystrophy Locus:

The following methods were used for the construction and analysis of radiation-reduced hybrids for use in the identification of the myotonic dystrophy gene. One hybrid, 2F5, contains 2–3 megabases of human material, derived exclusively from human chromosome 19 and includes markers which flank DM. DNA from this hybrid was used to construct genomic phage libraries from which 230 phage containing human inserts have been identified. Two other hybrids produced provide breakpoints within the interval covered by 2F5 and are useful in subdividing the phage clones into three groups.

Cell Culture

Cell line 20XP3542-1-4 was used as the parental cell line in two different X-irradiation experiments.
1. X-irradiation of 5000 rads followed by fusion to DNA repair deficient hamster cell line UV20 and selection with mitomycin C and polio virus.
2. X-irradiation of 5000 rads followed by fusion to HPRT negative hamster cell line Wg3h and selection in medium containing HAT (Hypoxanthine, Aminopterin and Thymidine) for clones which retained the HPRT gene and other material from the parental cell line.

Routinely, cells were grown in minimal essential medium with 10% fetal calf serum, penicillin and streptomycin (Northumbria Biologicals Ltd., Great Britain). In each experimental group, three lots of $10^7$ cells were irradiated using a $Cs^{137}$ source (0.66 Mev; 0.9 Gy/min). Irradiated cells were fused with $10^7$ UV20 cells in experimental group '1' and to $10^7$Wg3h cells in experiment '2'. Each fusion was split to ten 75 cm dishes and exposed to selective media twenty four hours post irradiation. In group '1', cells were selected in a final concentration of 0.01 ~M mitomycin C (Sigma Chemicals). For group '2', selection was performed with 1×HAT medium (from a 100× concentrate; Flow Laboratories, Great Britain). Twelve to twenty days post-irradiation, two to three surviving clones were picked from each dish using metal cloning rings and transferred to 24 well tissue culture plates (Costar). In experiment '1', cells surviving exposure to polio virus were grown up to 2×75 $cm^2$ flasks. One flask was used for DNA extraction and the other was frozen down. In experiment '2', duplicate clones were grown in parallel and one flask exposed to polio virus, using the procedure described previously (Brook, J. D. et al., *Genomics* 1:320–328 (1987)). For those clones killed by polio virus the duplicates were grown up and DNA extracted for analysis and cells frozen.

DNA Techniques

Southern blotting, filter hybridizations and probe labelling were performed according to standard procedures (Sambrook, et al., "Molecular Cloning—A Laboratory Manual". Cold Spring Harbor Press, 1989). Probes containing human repeat sequences were pre-annealed for five hours with a 1000-fold excess of sheared, unlabelled human DNA.

Cell line DNAs were analyzed with twenty-three DNA markers which were either positive in or derived from parental cell line 20XP3542-1-4. These were divided into two series.

Series 1 DNA markers included BCL3, APOC2, CKM, ERCC1, NE16, pD26 (D17S243) and pD48 (D8S42).

Series 2 DNA markers include pD3 (D19S61), pD8 (D19S62), pD10 (D19S63), pD36 (D19S64), pNE17, pD50 (D17S247), pD13 (D17S245), pD38 (D8S81), pD48 (D8S82), pD47 (D8S83), pD51, pD78, pD55, pD32, pD67 and pD41. The phage for which D-S numbers have been assigned are described in Brook, et al. and Harley, et al. (Brook, J. D. et al., *J. Med. Genet.* 28:84–88 (1991); Harley, H. G. et al., *Hum. Genet.* 87:73–80 (1991)). The probe defining locus D19S51 (p134C) was described by Johnson, K. et al., *Am. J. Hum. Genet.* 46:1073–1081 (1990).

Library Construction and Screening

A genomic DNA library was constructed from cell line 2F5 in vector Lambda DASH (Stratagene) by partial MboI digestion of cell line DNA, size selection of 15–25 Kb fragments on low melting point agarose gels and cloning into the BamHI site of the vector. Recombinants were plated on bacterial strain NM542 and screened with total human DNA. Southern blots were prepared from DNA of 35 phage digested with restriction enzymes BamHI, EcoRI, HindIII and SalI and hybridized with human DNA. Those bands not hybridizing well with human DNA were identified and excised from LMP agarose gel containing digests of the same phage and hybridized against mapping filters. These consisted of six lanes: Human, Hamster, 5B3, 3A3, GM89A99c7 and PK-87-19. Cell lines 5B3 and 3A3 are described in the results section. PK-87-19 contains a single chromosome 19 as its only human chromosome and GM89A99c7 contains the region 19q13.3-19qter plus chromosomes 3, 4, 7, 11, 18, 21, 22 and Xpter-Xq24.

Pulse Field Gel Electrophoresis

For analytical and preparative pulsed-field gel electrophoresis (PFGE), a Biorad CHEF-DRII apparatus was used. Pulse times were ramped from 40 to 200 or from 50 to 300 seconds, and the gels were run at 160 volts for 42 or 46 hours, with a buffer temperature of 15° C. The gels were 1% agarose or 5% low melting-point agarose (Gibco-BRL) for preparative gels. Samples of DNA from human white blood cells (female) and 2F5 and 20XP3542-1-4 hybrid cell-lines were prepared in agarose blocks as described previously (Shaw, D. J. et al., Hum. Genet. 83:71–74 (1989)) and digested with rare-cutter restriction enzymes.

Phage lambda libraries were constructed from DNA fractionated by preparative PFGE. Approximately 100 μg (16 blocks) of 2F5 hybrid DNA was digested with NotI and separated by PFGE. After electrophoresis, the outside lanes containing size markers were cut off and stained with ethidium bromide. The gel was re-assembled and the central section containing the fractionated hybrid cell line DNA, was cut into 2 mm slices at right angles to the direction of electrophoresis. These were melted at 65° C., cooled to 37° C. and the agarose was removed by digestion with agarose followed by phenol and chloroform extraction. The DNA was recovered by ethanol precipitation, a small aliquot of each fraction was digested with Pst1, the samples were separated by standard gel electrophoresis, blotted and hybridized with various probes to determine in which fractions the corresponding NotI fragments were present.

DNA from the chosen fractions was then partially digested with MboI to 15–25 kb average size. Due to the small amount of DNA available, the partial digest conditions were established by electrophoresis of the trial samples in 0.6% agarose gels, followed by blotting and hybridization with labelled Chinese hamster DNA. The partial digests were cloned in two ways: firstly, using lambda EMBL3 cut with BamHI in order to obtain MboI fragments internal to the original NotI fragment; and secondly, with a derivative of lambda EMBL3 in which one of the BamHI cloning sites was replaced with a NotI site. This allowed the ends of the NotI fragment to be obtained. The ligated DNAs were packaged in vitro and plated on *E. coli* strain ER1458. Phage with human inserts were identified by hybridization with labelled total human DNA.

In Situ Hybridization

DNA from 2F5 cells was prepared in agarose plugs for use as PCR template (van Omen, G. J. B. and Verkerck, In: *Human Genetic Diseases, A Practical Approach* IRL Press, Oxford (1986)). PCR primers (Alu-1 and Alu-2) that specifically recognize human consensus sequences located at the 5' and 3' ends of Alu segments, were used together with 2F5 template to amplify human unique sequences (Liu, et al., submitted). Alu-1 and Alu-2 sequences were GGATTA-CAGGYRTGAGCCA (SEQ ID NO:13) and RCCAYTG-CACTCCAGCCTG (SEQ ID NO:14) respectively, where Y is either pyrimidine (T or C) and R is either purine (A or G). 1 μg of PCR product was labelled with biotin-7-dATP using a nick translation kit (BRL cat. no. 8160SB). Free nucleotides were removed by passing the mixture through a Worthington Sephadex column. The procedure of Pinkel, et al. was followed for in situ hybridization with modifications described in Doll, et al. (Pinkel, D. et al., *Proc. Natl. Acad. Sci.* USA 83:2934–2938 (1986); Doll, G. et al., *Genes, Chromosomes and Cancer* 3:48–54 (1991)). Slides were viewed with a Zeiss epi-illumination photoscope with a filter combination 48 77 09 and photographed on Kodak Ektachrome™ 160 with exposure times between 30 and 50 seconds.

EXAMPLE 2

Analysis of Cell Lines

Cell lines from each of the radiation treatment groups were analyzed with two different sets of DNA markers. Three cell lines in particular appeared very useful and formed the basis of further analyses. Cell line 2F5 had lost all the non-chromosome 19 derived markers present in the parent cell line 20XP3542-1-4. Furthermore, it had also lost the four most proximal markers from chromosome 19; PVS, BCL2, APOC2 and CKM, while retaining the other chromosome 19 markers including ERCC1 and p134C (D19S51) which flank DM.

Hybrid line 5B3 retained even fewer markers than 2F5, however, non-contiguous pieces of chromosome 19 were present in this case. CKM, which maps between APOC2 and ERCC1, was deleted from cell line 5B3 whereas these flanking loci were present. Marker p134C (D19S51), the closest marker flanking DM on the distal side, was also deleted from 5B3. Nevertheless, this cell line was useful for subdividing the region of chromosome 19 distal to ERCC1. Similarly, cell line 3A3 also provides a breakpoint within this interval. 3A3 had lost several of the distal chromosome 19 markers present in cell line 2F5, while retaining p134C (D19S51) and other more proximal chromosome 19 markers, as well as several of the nonchromosome 19 markers from the parent cell line. Thus, cell lines 3A3 and 5B3 provided a means of assigning DNA clones derived from cell line 2F5 into three intervals. Phage clones present in both 3A3 and 5B3 were assigned to interval 'A'. Those present in 3A3, but absent from 5B3, were assigned to 'B' and those absent from both 3A3 and 5B3 were assigned to interval 'C'.

EXAMPLE 3

Further Analysis of Cell Line 2F5

DNA from cell line 2F5 was labelled and used as a probe on mitotic spreads of human chromosomes. This hybridized to a single region from the long arm of chromosome 19.

The human DNA content was also characterized by PFGE. DNA from the hybrids 2F5 and 20XP3542-1-4 was digested with NotI, MluI and BssHII and separated by PFGE. A blot of the gel was hybridized with total human DNA. 2F5 has a considerably reduced human DNA content compared to its parent cell line. In the NotI digest, fragments hybridizing with human DNA of approximately 50, 180, 200, 400, 500, 1000 and 1300 kb were present. The largest fragment was not present in the parental cell line and was probably due to a translocation between the end of the human DNA in 2F5 and a hamster chromosome. In situ hybridization with labelled human DNA onto chromosome spreads of cell line 2F5 indicate that two such fragments should be present. The 1300 kb fragment is probably mostly hamster DNA. Furthermore, hybridization with single-copy probes showed that some of the other larger fragments were due to partial digestion. Based on the NotI digestion, it was estimated that the human DNA content of 2F5 is approximately 2 Mb.

EXAMPLE 4

Construction and Screening of Libraries from 2F5

Three different libraries were made from cell line 2F5. The first was a total genomic library constructed in lambda Dash. $3.5 \times 10^5$ recombinant phage were screened with human cot 1 DNA and 230 phage containing human inserts identified (approx. 0.06%). Given a diploid cell content of $4 \times 10^9$ base pairs, this should give a human DNA content of 2.5 megabases in general agreement with the estimates from PFGE.

Thirty-five clones were localized with a mini hybrid-panel and subdivided into three intervals; A, B and C. Eighteen clones, present in both hybrid cell lines 5B3 and 3A3, were assigned to interval A. Four clones mapped to cell line 3A3 but not 5B3 and were assigned to interval B, and thirteen mapped to neither 3A3 nor 5B3 and were assigned to interval C.

The other two libraries were constructed from PFGE fractionated DNA as described above. The marker D19S63 showed marked linkage disequilibrium and no recombination with the DM locus (Harley, H. G. et al., *Am. J. Hum. Genet.* 49:68–75 (1991)). In order to obtain more cloned DNA and identify potential coding sequences in the vicinity of this marker, libraries were constructed from the 200 kb NotI fragment identified by D19S63. A total of 45 human clones were isolated, 5 of which were NotI end clones. These numbers were reduced to 24 and 2, respectively, when duplicate clones were eliminated. One of the NotI end clones (lambda #5) was used to extend the PFGE map as described below. All of the clones were digested with SacII, an enzyme that generally cuts within HTF islands (Lindsay, S. and A. P. Bird, *Nature* 327:336–338 (1987)). Six clones with SacII sites were identified. The phage DNAs were subcloned into plasmids and the fragments containing the SacII sites were digested with HpaII. In all 6 cases, multiple HpaII sites were present, thus confirming that they represent genuine HTF islands.

Five of the HTF island subclones (p20.1, p36.1, 037.1, p42.3 and p56.1) gave unambiguous localizations on the PFGE map, and mapped to interval 'A' as defined above. Two of these clones (p20.1 and p36.1) were not on the same NotI fragment as D19S63. It is possible that the original NotI digest used in the library construction was incomplete, resulting in a contaminating 250 kb NotI fragment that was not completely resolved from the 200 kb fragment by the preparative PFGE. All of the HTF island subclones detected sequence conservation by zoo-blot analysis and were used to screen cDNA libraries.

EXAMPLE 5

Long Range Restriction Map of the DM Region

A number of single-copy probes from the libraries made from 2F5, together with some existing markers for this region, were used to complete the PFGE map of the DM region of chromosome 19. NotI and MluI were the sites principally used for the 2 enzymes. Probes containing or adjacent to NotI sites, obtained by selectively cloning the ends of NotI fragments, by chromosome walking or by screening phage clones by NotI digestion, were particularly useful in the construction of the map. Many of the sites identified showed partial digestion.

Part of the PFGE map has been previously reported. (Harley, H. G. et al., *Am. J. Hum. Genet.* 49:68–75 (1991)). In the data presented herein, the gap in the previous map by isolation of a NotI end clone (lambda #5) and the corresponding linking clone (lambda M23B) has been closed. A probe derived from the distal half of the latter identified the same 50 kb NotI fragment as does p36.1, which in turn identifies a 40 kb MluI fragment and a 450 kb partial digest MluI fragment. The 450 kb fragment was also identified by D19S51 (p134C). Since the latter marker was in interval 'B' as defined by X-ray hybrid mapping, and all of the former markers were in interval 'A', the breakpoint between intervals 'A' and 'B' must be within the 450 kb NotI fragment.

EXAMPLE 6

Sequence Conservation and cDNAs

Two of the clones identified in the initial genomic library screen, which map to interval A, lambda MW and lambda M2C showed hybridization to the rodent lane on southern blot analysis indicating sequence conservation. These clones were distinct from the HTF island clones described above. Fragments of each of these phage were screened against a muscle cDNA library and clones identified. Each of these clones was purified, sub-cloned and hybridized back to the mapping filters. Both cDNAs localize to 19Q13.3-19qter and map back to interval A of hybrid cell line 2F5. Human positive bands were present in cell lines 5B3, 3A3, GM89A99C7 and PK-87-19. Hamster bands were also present in 5B3, 3A3 and PK-87-19. The other bands in GM89A99C7 were derived from mouse.

In order to produce a cell line which will provide a source of DNA markers close to the DM locus, two traditional approaches were used. As a starting point, cell line 20XP3542-1-4 (Stallings et al., *Am. J. Hum. Genet.* 43:144–153 (1988)) which contains a single human element 20–30 megabases in size derived from at least four different chromosomes including a small part of 19q was used.

Of the two strategies adopted, group 1, in which the parental cell line was lethally irradiated and fused to DNA repair deficient cell line UV20 followed by selection of clones in mitomycin C and polio virus, produced the most useful clones, in particular 2F5. Data from both DNA marker analysis and in situ hybridization indicated that the human material present in one of these clones (2F5) was derived exclusively from a small region of 19q13. DNA from this cell line has been used for library construction and subsequent analysis. One other cell line from this group, 5B3, was also valuable as it provided a subdivision of the interval covered by 2F5.

A further useful cell line was produced in group 2. Hybrid 3A3 resulted from the exposure of the parental cell line to lethal dose irradiation followed by fusion to HPRT deficient hamster cells. As described by Cox et al. (1989), no selection was employed for the region of interest. Cell line 3A3, like hybrid 5B3 from group 1, lacked some of the markers distal to ERCC1. Together these hybrids have been used to subdivide this part of chromosome 19 into three intervals.

The hybrid 2F5 provided a source of DNA specific for the region of chromosome 19 distal to ERCC1. By pulsed field gel electrophoresis, it was estimated that the size of this region was 2000 kb, and a long range restriction map covering 1600 kb was constructed. Two lines of evidence suggest that the DM gene was located within this interval. Firstly, crossovers have been reported between ERCC1 and DM, and between D19S51 and DM, indicating that the order of markers is ERCC1-DM-D19S51 (Johnson et al., (1990); Smeets et al., (1991)). Both of these markers flanking DM were present in the 2F5 hybrid cell line. Secondly, it had been shown that there is a strong linkage disequilibrium between DM and D19S63, but a lack of disequilibrium between DM and either ERCC1, CKM, D19S51 or D19S62 (Harley et al., (1991); Johnson et al., (1990)). Of all the markers used in linkage analysis with DM, D19S63 was apparenting the closest to the DM gene. Thus, these results indicated that D19S63 was located between ERCC1 and D19S51.

Because of the localization of the flanking markers ERCC1 and D19S51 to intervals A and B respectively, it was reasonable to determine that the DM gene could be located within either or both of these intervals. Twenty seven phage clones were derived from 2F5 libraries mapped to intervals A and B. These clones were used to form a single contig across this interval by chromosomal walking from multiple points using the other human clones described herein, identified from the 2F5 libraries. With this information, it is was possible to screen for conserved sequences and to identify fetal muscle, fetal brain and adult brain cDNA clones, that were tested by DNA sequencing and mutational analysis as candidates for the DM gene. The full-length DNA sequence of the DM gene was determined and is shown in FIG. 6A–6J (SEQ ID NO:10), along with the deduced amino acid sequence (SEQ ID NO:11). Also indicated on FIG. 6A–6J (lines and arrows) are the locations of two cDNAs comprising the gene sequences, cDNA 41 and cDNA 28.

Figure 7:
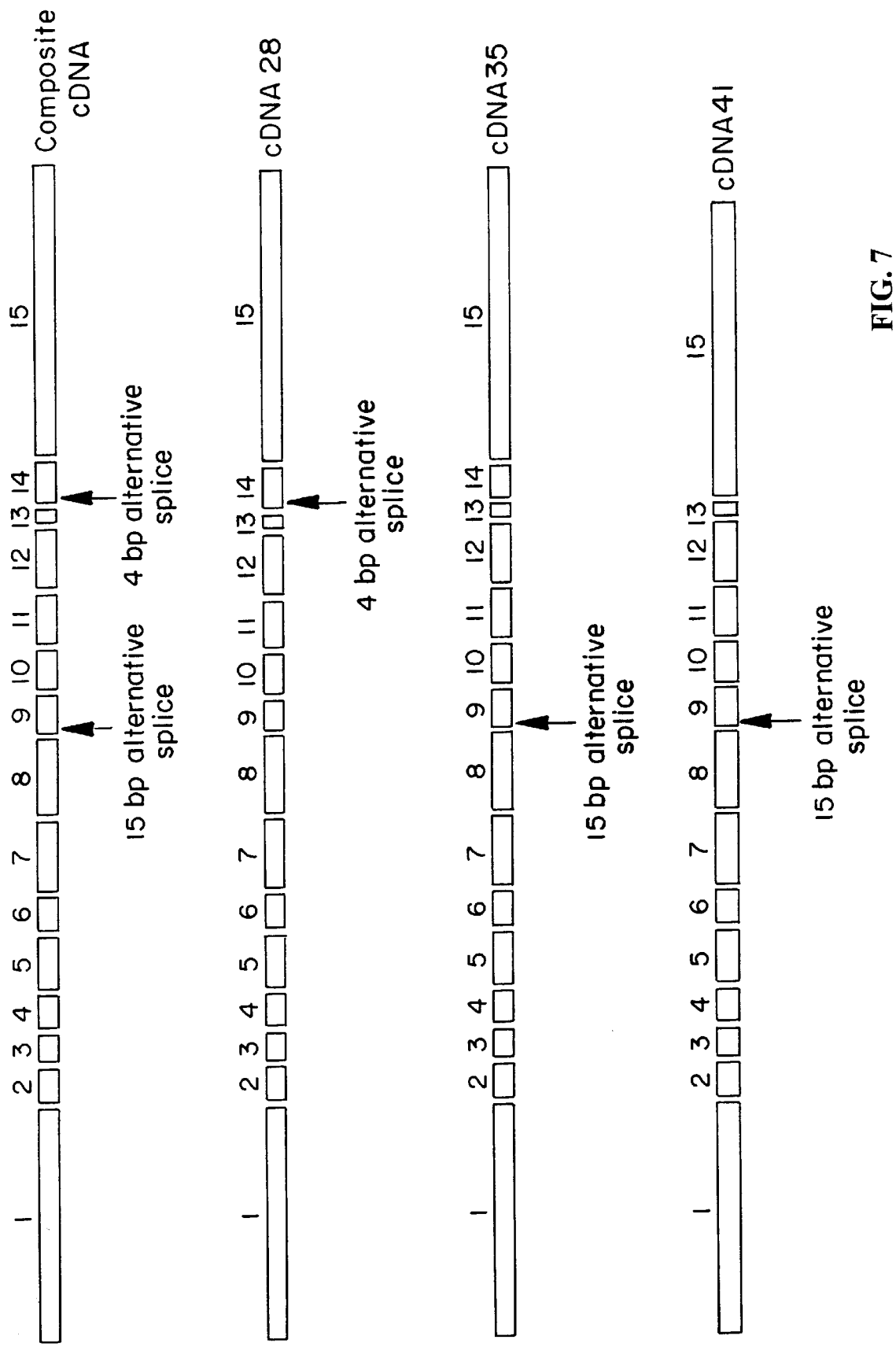
FIG. 7 is a graphic representation of the alternate splice sites of the DM gene and of the resulting cDNAs.

As shown in FIG. 7, DNA sequence analysis of multiple cDNA clones identified several DM gene variants, suggesting that the DM gene message undergoes alternative splicing. For example, cDNA 28 (isolated from an adult brain library) contains 4 bases at the 5' end of exon 14 which are not present in either cDNA 35 (from fetal brain) or 41 (from fetal muscle). Alternatively, both cDNA 35 and 41 contain 15 bases at the 5' end of exon 9 which are not present in cDNA 28. Finally, cDNA 41 does not contain exon 14. These data reasonably imply that structurally distinct forms of the DM kinase are expressed, possibly in a temporal, tissue-specific, or disease-specific pattern. The clones reported here can also be used to test for the presence of coding sequences using the exon-amplification technique of Buckler et al., *PNAS* 88:4005–4009 (1991)).

GROUP B

Isolation of the DNA sequence

Clone λM10M was found to have the ability to distinguish between DM patients and normal individuals, as follows. A fragment of the DNA from clone λM10M was radioactively labelled to make a "DNA probe". A series of DNA samples from DM patients and normal individuals were digested with EcoRI into specific small fragments. The fragments were separated according to their length by electrophoresis in an agarose gel, and transferred to a nylon membrane to which they adhere (Southern blotting). The radioactive probe from λM10M was then incubated with the membrane, which allows it to find its corresponding sequence in each of the samples of human DNA (DNA hybridization). The positions of these fragments corresponding to λM10M are always larger (by varying amounts) in DM patient DNAs than in DNAs from normal individuals. Following confirmation on a larger number of samples, it was apparent that λM10M contained a copy of the DNA sequence responsible for myotonic dystrophy.

The original λM10M clone was derived from DNA of complete human chromosomes. Because only part of this DNA is "expressed" (i.e. functions as genes by making proteins), a second cloned sequence was obtained using λM10M as a probe. This second clone came from a collection of cDNAs representing most of the genes expressed in human brain. The clone contains 2726 bases of human DNA as shown in FIG. 8A and 8B. The entire DNA sequence was determined and is shown in (SEQ ID NO:12). The position of the 3-base repeat that undergoes expansion in DM patients is indicated and lies at a position approximately 500 bp from the poly(A) tract of a mRNA expressed in many of the tissues affected in DM. The RNA in which the repeat resides encodes a polypeptide with strong amino acid homology to members of the protein kinase gene family.

Analysis of human DNA samples for the DM mutation

Two different but complementary methods are used to determine the presence of the DM mutation and the size of the expanded sequence. These procedures may be performed on DNA samples from human blood, mouthwashes, or chorion villus biopsies. All of the methodology is based on standard molecular genetic laboratory procedures (Sambrook J., Fritsch E. R., Maniatis T. "Molecular cloning—a laboratory manual", Cold Spring Harbor Press, 1989).

GROUP B EXEMPLIFICATION

EXAMPLE 7

Experimental Procedures

Southern Blots

The first method is based on Southern blotting and hybridization, and is most effective in detecting expanded sequences towards the upper end of the size range. Samples (5–10 μg) of DNA from people to be tested, together with normal controls, are digested by incubation with the restriction enzyme EcoRI or PstI for 2–4 hours at 37° C. The samples are then separated by electrophoresis in 0.8% agarose gels for 16–18 hours at 45 volts, and the DNA transferred to a nylon membrane by overnight capillary action (Southern blotting). The membrane is removed from the agarose gel, dried, and the DNA fixed to it by ultraviolet radiation. A probe is consisting of a part of the clone sequence (SEQ ID NO:12) was made by incorporation of a radioactive tracer into the DNA sequence. This was then incubated overnight at 65° C. with the membrane in an aqueous buffer solution, allowing the probe to hybridize to the DNA samples on the membrane. The excess unbound probe was then washed off with dilute salt solution at 65° C., and the membrane exposed to X-ray film in the dark at −70° C. for 1 to 4 days. The film was developed and aligned with the original membrane, allowing identification of the various samples and the size of the DNA fragments containing the 3-base repeat sequence.

Using the Southern blotting technique genomic DNA was digested with EcoRI and then probed with pBBO.7, a single copy sub-clone of λM9C.

PCR Analysis

The second procedure is based on PCR (polymerase chain reaction) and is best suited to the detection of DM mutations that are only slightly larger than normal. A pair of small, unique DNA sequences called "Primers", which are derived from the clone sequence and flank closely the site of the 3-base repeat, are used. Small samples (0.1–0.5 μg) of DNA from individuals to be tested, along with normal controls, are mixed with 20 pmoles of each primer, 1 unit of a bacterial enzyme (Taq polymerase), individual bases for DNA synthesis, and buffer salts, in a volume of 20 μL. The mixtures are then subjected to a cyclical, 3-phase incubation protocol. In the first phase the mixture is heated to 94° C. for 90 seconds to separate the two strands of the DNA sample. The second phase is for 60 seconds at 62° C. and allows the primers to bind to their complementary sites on the sample DNA. During the third phase (2 minutes at 72° C.) the Taq polymerase enzyme synthesizes a new complementary DNA strand on each of the sample strands, starting from the primer. The whole 3-phase procedure is repeated 30 times, using an automatic programmable heating/cooling device. Because each cycle causes a doubling of the number of molecules, the net result is to specifically amplify the sequence delimited by the two primers. In our procedure this represents the 3-base repeat region which is expanded in DM patients. The products of the PCR reactions are separated by agarose gel electrophoresis (3% agarose gel, 2 hours at 80 volts) and visualized by staining the DNA with a fluorescent dye. The sizes of the amplified fragments are estimated by comparison with known standards, separated on the same electrophoresis gel.

It will be understood that variations of the above methods are possible. For example, SEQ ID NO:12 is a cDNA (RNA derived) sequence, and there are flanking and intervening sequences mixed in with this in genomic DNA. Suitable PCR primers which flank the CTG repeat regions in genomic DNA may also be used which may differ from those described above.

EXAMPLE 8

Transmission of CTG Repeat through Successive Generations

Figure 9A:
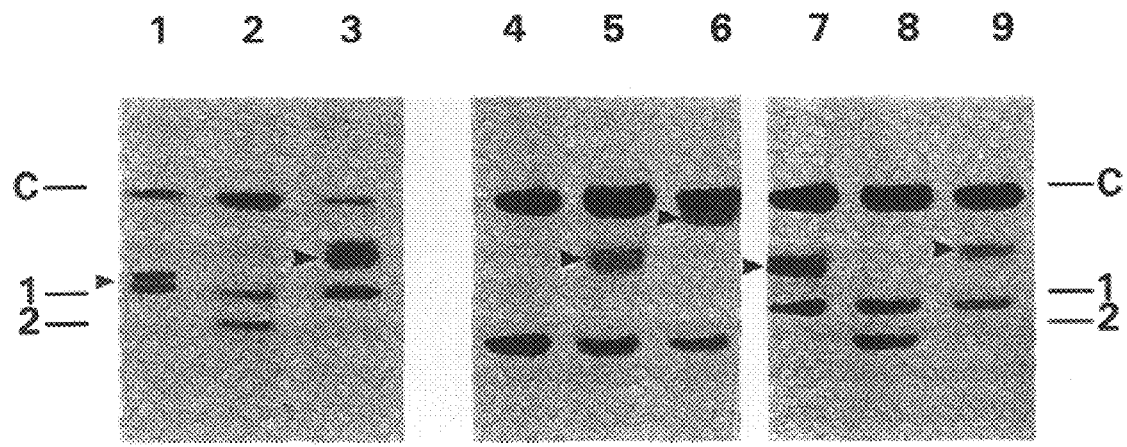
FIGS. 9A–9B are autoradiographs showing the variation of fragment lengths for a number of individuals of Group B.
Figure 9B:
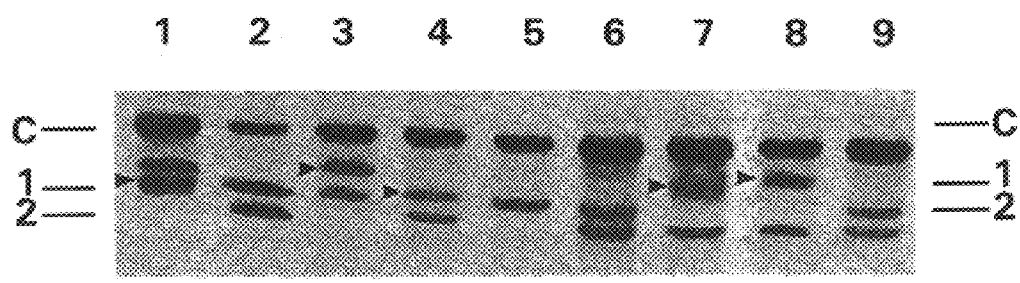

From FIG. 9A–9B it is evident that all individuals have a constant ~15 kb band (c). Normal individuals are either homozygous or heterozygous for bands of 10 and 9 kb (alleles 1 and 2). Affected individuals have one of these two bands plus a second band >10 kb, indicated by ▶ in FIGS. 9A and 9B.

In FIG. 9A, lanes 2, 4 and 8 are normal, unrelated individuals; lanes 1, 5 and 7 are unrelated affected individuals; lanes 3, 6 and 9 are affected offspring of individuals 1 and 2, 4 and 5, 7 and 8 respectively. Lane 1 shows one of the smallest size changes detectable, and lane 6 one of the largest. Two distinct bands can clearly be seen on the autoradiograph. Lanes 5 and 7 illustrate the smearing of bands seen in some individuals.

Figure 9C:
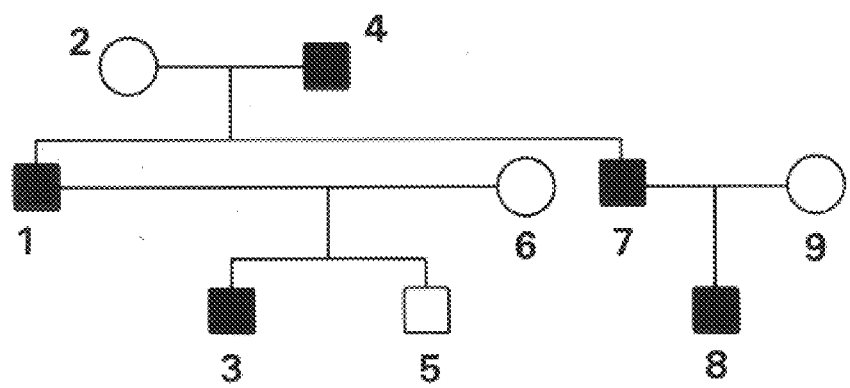
FIG. 9C is a family tree for the individuals of FIG. 9B.

In FIG. 9B, individual 4 is classified as late onset and has a novel fragment minimally larger than the normal 10 kb band. His two affected offspring are classified as adult onset (individual 1 has a minimally increased fragment) and early adult onset (individual 7 with a novel fragment ~1 kb larger than that of his father). The affected grandchildren (individuals 3 and 8) are both classified as early onset can be seen to have a much larger fragment than their respective parents and their grandparents. Individual 8 had the earliest age at onset and is the most severely affected and also has the largest fragment in this family. FIG. 9C is a family tree showing the transmission of the CTG repeat unit among the individuals of FIG. 9B.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A nucleotide sequence selected from the group consisting of:
   a) isolated DNA obtained from human chromosome 19, wherein said DNA consists of the myotonic dystrophy gene including a variable number of repeats of the three-base unit CTG or the substantially complementary strand of said DNA, wherein the number of repeats is greater than about 50 in individuals affected by myotonic dystrophy,
   b) isolated RNA transcribed from the DNA of a); and
   c) a fragment of the nucleotide sequences of a) or b) which comprises a region of DNA containing the CTG variable repeat region of the myotonic dystrophy gene, wherein said fragment specifically hybridizes to the CTG variable repeat region of the nucleotide sequences of a) or b).

2. The nucleotide sequence according to claim 1 consisting of SEQ ID NO:8, or the substantially complementary strand of SEQ ID NO:8.

3. The nucleotide sequence of claim 1 which encodes a protein kinase.

4. The nucleotide sequence of claim 3 which encodes an amino acid sequence sequence selected from the group consisting of SEQ ID NO:9 and SEQ ID NO:11.

5. A nucleic acid hybridization probe useful for determining the number of repeats of the three-base unit in the nucleotide sequence of claim 1, wherein the probe specifically hybridizes to:
   a) the CTG repeat region of the nucleotide sequences of claim 1;
   b) a substantially complementary strand of a); or
   c) a fragment of either a) or b), wherein the fragment comprises the CTG repeat region.

6. The nucleic acid hybridization probe of claim 5 consisting of SEQ ID NO:8 or the substantially complementary strand of SEQ ID NO:8.

7. The nucleic acid hybridization probe of claim 5 consisting of a fragment of a nucleotide sequence selected from the group consisting of SEQ ID NO:8 and the substantially complementary strand of SEQ ID NO:8, the fragment being of sufficient length and specificity to specifically hybridize to SEQ ID NO:8 or the substantially complementary strand of SEQ ID NO:8.

8. Primers that amplify at least the variable repeat region of the nucleotide sequence of claim 1.

9. Primers according to claim 8, comprising first and second oligonucleotides closely flanking said repeat region, said first and second oligonucleotides each comprising from 8 to 32 bases.

10. An isolated human DNA sequence obtained from human chromosome 19, wherein said DNA consists of the myotonic dystrophy gene comprising the CTG triplet repeat region of the myotonic dystrophy gene, or the substantially complementary strand of said DNA, wherein the CTG triplet is repeated about 50 times or more.

11. The primers according to claim 8 selected from the group consisting of: SEQ ID NO:1; SEQ ID NO:2; SEQ ID NO:3; SEQ ID NO:4; SEQ ID NO:5 and SEQ ID NO:6, or their substantially complementary strands.

12. A primer according to claim 8 wherein the primer is selected from the group consisting of SEQ ID NO:7, the substantially complementary strand of SEQ ID NO:7, a fragment of SEQ ID NO:7, and the substantially complementary strand of the fragment of SEQ ID NO:7.

13. A pair of oligonucleotide primers for amplifying the CTG variable repeat region of a myotonic dystrophy gene wherein each primer consists of a fragment of SEQ ID NO:8 which flanks the CTG variable repeat region of the gene or the substantially complementary stand of the fragment of SEQ ID NO:8.

14. An isolated nucleic acid sequence comprising a CTG variable reseat region which specifically hybridizes to a restriction fragment of a myotonic dystrophy gene containing the CTG variable repeat region.

15. An isolated nucleic acid sequence selected from the group consisting of:
   a) SEQ ID NO:8;
   b) the substantially complementary strand of SEQ ID NO:8;
   c) nucleic acid sequences comprising a CTG variable repeat region that specifically hybridize to the CTG variable reseat region of SEQ ID NO:8; and
   d) RNA transcribed from SEQ ID NO:8.

* * * * *